(12) United States Patent
Bigeleisen et al.

(10) Patent No.: US 12,193,874 B2
(45) Date of Patent: Jan. 14, 2025

(54) THERMO-RESPONSIVE ULTRASOUND COUPLING GEL, AND METHODS AND USES THEREOF

(71) Applicant: UNIVERSITY OF MARYLAND, BALTIMORE, Baltimore, MD (US)

(72) Inventors: Paul E. Bigeleisen, Baltimore, MD (US); Kyle Kenney, Baltimore, MD (US); Mark E. Shirtliff, Ellicott City, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 1152 days.

(21) Appl. No.: 16/978,065

(22) PCT Filed: Mar. 6, 2019

(86) PCT No.: PCT/US2019/020969
§ 371 (c)(1),
(2) Date: Sep. 3, 2020

(87) PCT Pub. No.: WO2019/173486
PCT Pub. Date: Sep. 12, 2019

(65) Prior Publication Data
US 2021/0153841 A1    May 27, 2021

Related U.S. Application Data

(60) Provisional application No. 62/639,156, filed on Mar. 6, 2018.

(51) Int. Cl.
*A61B 8/00* (2006.01)
*A61K 47/32* (2006.01)
*A61K 47/38* (2006.01)
*A61K 49/22* (2006.01)

(52) U.S. Cl.
CPC ............ *A61B 8/4281* (2013.01); *A61K 47/32* (2013.01); *A61K 47/38* (2013.01); *A61K 49/226* (2013.01)

(58) Field of Classification Search
CPC .................. A61K 41/00; A61B 8/00
See application file for complete search history.

(56) References Cited

U.S. PATENT DOCUMENTS

| | | | | |
|---|---|---|---|---|
| 2005/0074407 | A1* | 4/2005 | Smith | A61K 49/222 424/9.5 |
| 2012/0016236 | A1* | 1/2012 | Wiley | C08L 71/02 600/437 |
| 2012/0020932 | A1* | 1/2012 | Yao | A61K 9/0024 514/17.2 |

FOREIGN PATENT DOCUMENTS

| | | | |
|---|---|---|---|
| CN | 1304441 | | 3/2007 |
| CN | 104721131 | | 6/2015 |
| CN | 105310982 | | 2/2016 |
| WO | WO 2017087606 | * | 5/2017 |
| WO | WO-2017087606 A1 | * | 5/2017 |

OTHER PUBLICATIONS

G. Staikos et al., Synthesis and Aqueous Solution Properties of Novel Thermoresponsive Graft Copolymers Based on a Carboxymethylcellulose Backbone, Macromolecules, 34, 4958-4964. (Year: 2001).*
Sun I Kim et al., Synthesis and characteristics of interpenetrating polymer network hydrogels composed of poly(vinyl alcohol) and poly(N-isopropylacrylamide), Reactive and Functional Polymers, 55, 61-67. (Year: 2003).*
International Search Report issued May 23, 2019, in International (PCT) Application No. PCT/US2019/020969.
Written Opinion of the International Searching Authority mailed May 23, 2019, in International (PCT) Application No. PCT/US2019/020969.
International Preliminary Report on Patentability issued Sep. 8, 2020, in International (PCT) Application No. PCT/US2019/020969.

* cited by examiner

*Primary Examiner* — Michael G. Hartley
*Assistant Examiner* — Jagadishwar R Samala
(74) *Attorney, Agent, or Firm* — WENDEROTH, LIND & PONACK, L.L.P.

(57) ABSTRACT

A thermo-responsive ultrasound coupling gel that contains a thermo-responsive polymer such as poly(n-isopropyl acrylamide), the gel having a phase shift at a temperature in the range of 32 to 35° C. such that the gel has a loss factor G"/G' of >1 at <32° C. and a loss factor G"/G' of <1 at >35° C. The gel can also contain at least one of a solvent and gelling agent. Methods and uses for the thermo-responsive ultrasound coupling gel in an ultrasound and/or ultrasound guided procedure.

11 Claims, 22 Drawing Sheets

FIG. 1(a)
FIG. 1(b)
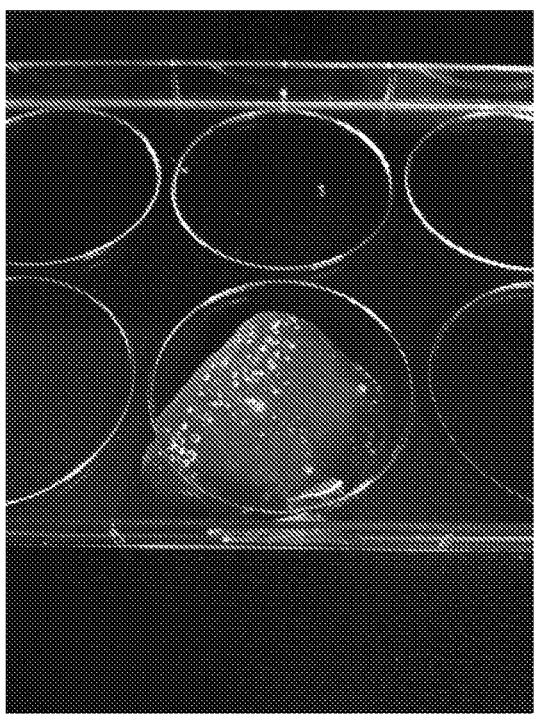
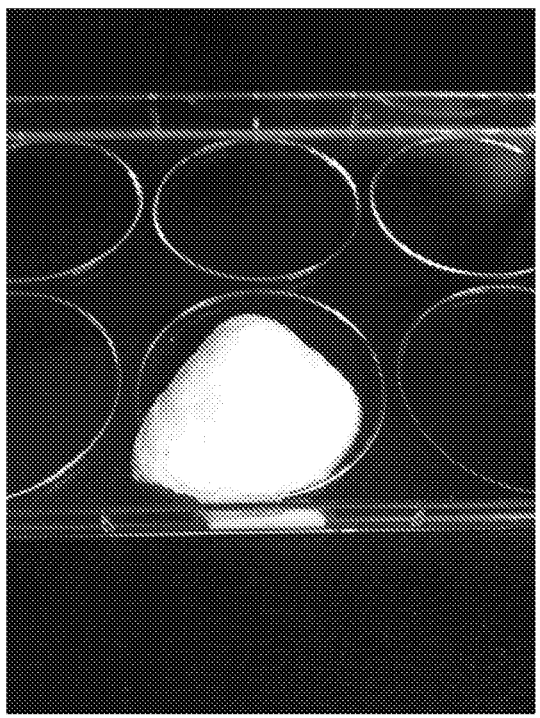

THERMO-RESPONSIVE ULTRASOUND COUPLING GEL, AND METHODS AND USES THEREOF

TECHNICAL FIELD

The present application relates to thermo-responsive ultrasound coupling gels, and related methods and uses of such thermo-responsive ultrasound coupling gels. The thermo-responsive ultrasound coupling gels can be applied by a practitioner in a state that initially is slippery to allow for easy ultrasound scanning, but becomes sticky after a short period of time to inhibit drift of the ultrasound probe. The thermo-responsive ultrasound coupling gels can be beneficially used, for example, in ultrasound-guided procedures.

BACKGROUND

In the field of medical imaging, "ultrasound" is common technique that utilizes ultrasound waves to produce images from the inside of a body, such as a human or animal body. An ultrasound procedure typically involves an ultrasound probe (i.e., transducer) being placed on the skin by a sonographer. The ultrasound probe emits ultrasound waves into the body, and detects the soundwaves reflected back to the ultrasound probe. The emission and detection of such soundwaves produces electrical signals that can be translated into images of the inside of the body.

A gel can be placed between the body and the ultrasound probe that couples the body and the ultrasound probe. The gel acts to prevent the formation of air pockets between the body and the ultrasound probe, inter alia. Such air pockets can impede the emission and detection of soundwaves by causing acoustical interferences, and can inhibit the effective production of images produced by the "ultrasound" technique. Thus, such coupling ultrasound gels can be used to minimize acoustical interferences with the emission and detection of soundwaves, thereby allowing ultrasound waves to transfer into the body and back to the ultrasound probe with reduced levels of energy loss and acoustical interferences.

In addition to providing an appropriate acoustical medium for the ultrasound, ultrasound gels lubricate the surface of the skin to allow the ultrasound probe to glide on the surface of the skin. Easy movement of the probe on the skin during an ultrasound procedure allows for targeting of the correct tissue sites within the body. However, the slick nature of standard ultrasound gels having low adhesivity (i.e., tack) allows for the unintentional movement of the ultrasound probe on the skin of a patient during the course of the procedure, which is referred to as drift. Drift can cause difficulties when trying to maintain position of the ultrasound probe.

Although "ultrasound" techniques can include non-invasive techniques that occur on the surface of the skin of the body, some techniques utilize the images from an ultrasound as a guide for more invasive procedures. For instance, an ultrasound-guided biopsy can be used to obtain tissue samples via a biopsy needle. In an ultrasound-guided biopsy, the ultrasound allows the practitioner to accurately harvest cells from specific organs and locations in a patient using a biopsy needle together with the ultrasound. Drift can be problematic when attempting to keep the biopsy needle under the probe beam, thereby leading to malposition of the needle tip relative to the biopsy site. Similar problems can occur in, for example, procedures involving a cannulation or injection site.

Further, commercially available ultrasound gels can be pressure sensitive, whereby the ultrasound probe glides more easily when pressure is applied. Since the sonographer may adjust the pressure of the ultrasound probe during the procedure, the change is pressure can also cause problematic drift.

Based upon the above-described problems with commercially available ultrasound gels, the inventors have developed a novel, thermo-responsive coupling gel that inhibits drift, inter alia. The thermo-responsive coupling gel described herein behaves as an elastic solid with low tack at increased temperatures (e.g., ≥35° C.), wherein the gel is slippery and used for ultrasound scanning and positioning. As the gel cools to skin temperature (i.e., ~32 to 34° C.), the gel becomes a viscoelastic liquid with increased tack, wherein drift is reduced thereby allowing the practitioner to accurately guide a needle tip to the target of interest. The thermo-responsive coupling gel is substantially unchanged by pressure so that the probe does not glide more easily when pressure is applied to the probe. The decreased drift can improve the efficacy of all ultrasound guided procedures, such as nerve blocks, nerve block catheters, biopsy of the liver and kidneys, cannulation of all arteries and veins, etc. Even though ultrasound is typically used in medical imaging, the thermo-responsive coupling gel described herein can also be used in industrial applications, such as machinery inspections.

BRIEF SUMMARY

In view of the above-mentioned exemplary problems with conventional and known ultrasound coupling gels and methods, the present application provides novel thermo-responsive ultrasound coupling gels, and associated methods and uses.

In a first embodiment, the thermo-responsive ultrasound coupling gel comprises a thermo-responsive polymer, wherein the gel has a phase shift at a temperature in the range of 32 to 35° C. such that the gel has a loss factor $G''/G'$ of >1 at <32° C. and a loss factor $G''/G'$ of <1 at >35° C. The thermo-responsive ultrasound coupling gel can further comprise at least one of a solvent and a gelling agent. The thermo-responsive polymer can be poly(n-isopropyl acrylamide). The solvent can be selected from the group consisting of water, alcohols, and mixtures thereof. The gelling agent can be selected from the group consisting of cellulose polymers, synthetic polymers, natural polymers, semi-synthetic polymers, and mixtures thereof. The solvent can be polyvinyl alcohol. The gelling agent can be present is hydroxy(propylmethyl) cellulose. The thermo-responsive ultrasound coupling gel can further comprises an additional component selected from the group consisting of preservatives, antioxidants, fragrances, humectants, oils, emulsifiers, colorants, thickeners, stabilizers, binders, texturizers, pH control agents, and mixtures thereof.

Further, the thermo-responsive ultrasound coupling gel can comprise a thermo-responsive polymer solution that comprises 1-10 wt. % of the thermo-responsive polymer, and water, a solvent solution that comprises 10-30 wt. % of the solvent, and water, and a gelling agent solution that comprises 10-30 wt. % of the gelling agent, and water. The thermo-responsive ultrasound coupling gel can also comprise a thermo-responsive polymer solution that comprises 3-5 wt. % of the thermo-responsive polymer, and water, a solvent solution that comprises 16-18 wt. % of the solvent, and water, and a gelling agent solution that comprises 19-21 wt. % of the gelling agent, and water. The thermo-responsive ultrasound coupling gel can even further comprise a thermo-responsive polymer solution that comprises 4 wt. % of the thermo-responsive polymer, wherein the thermo-responsive polymer is poly(n-isopropyl acrylamide), and water, a solvent solution that comprises 17 wt. % of the solvent, wherein the solvent is polyvinyl alcohol, and water, and a solvent solution that comprises 20 wt. % of the gelling agent, wherein the gelling agent is hydroxy(propylmethyl) cellulose, and water. The weight ratio of the thermo-responsive polymer solution to the solvent solution to the gelling agent solution can be 4-1:4-1:4-1 to 1:1:1. The thermo-responsive ultrasound coupling gel has a tack at ≤32° C. that is ≥20% of a tack at ≥35° C.

In a further embodiment, a method of conducting an ultrasound comprises a) heating the above-mentioned thermo-responsive ultrasound coupling gels to a temperature≥35° C.; and then b) applying the thermo-responsive ultrasound coupling gel to a patient. The thermo-responsive ultrasound coupling gel can also be applied to the patient at a temperature≥35° C. The method can further comprise c) cooling the thermo-responsive ultrasound coupling gel to a temperature<35° C. Also, the method can further comprise d) performing an ultrasound guided procedure, wherein the thermo-responsive ultrasound coupling gel is at a temperature<35° C. The thermo-responsive ultrasound coupling gel can have a tack in step d) that is ≥20% of a tack in step a). In the method, the thermo-responsive ultrasound coupling gel can comprise a thermo-responsive polymer solution that comprises 4 wt. % of the thermo-responsive polymer, wherein the thermo-responsive polymer is poly(n-isopropyl acrylamide), and water, a solvent solution that comprises 17 wt. % of the solvent, wherein the solvent is polyvinyl alcohol, and water, and a solvent solution that comprises 20 wt. % of the gelling agent, wherein the gelling agent is hydroxy(propylmethyl) cellulose, and water, and wherein the weight ratio of the thermo-responsive polymer solution to the solvent solution to the gelling agent solution is 1:1:1.

Additionally, in a further embodiment, the use of each of the above-mentioned embodiments of the thermo-responsive ultrasound coupling gels is provided for use as an ultrasound coupling gel. Each of the above-mentioned embodiments of the thermo-responsive ultrasound coupling gels is also provided for use in an ultrasound procedure. Finally, each of the above-mentioned embodiments of the thermo-responsive ultrasound coupling gels is provided for use in an ultrasound guided procedure.

Other objects, features and advantages of the present invention will be apparent to those of ordinary skill in the art in view of the following detailed description of the invention and accompanying drawings.

BRIEF DESCRIPTION OF THE DRAWINGS

The drawings as provided for herein include some exemplary embodiments related to the thermo-responsive ultrasound coupling gels, methods, and uses of the present application, the detailed description of which follows. The drawings are merely exemplary, and are clearly not intended to limit the invention.

FIG. 1(a) is a picture showing an embodiment of the thermo-responsive ultrasound coupling gel before exposure to heat.

FIG. 1(b) is a picture showing an embodiment of the thermo-responsive ultrasound coupling gel after exposure to heat.

DETAILED DESCRIPTION

Figure 2A:
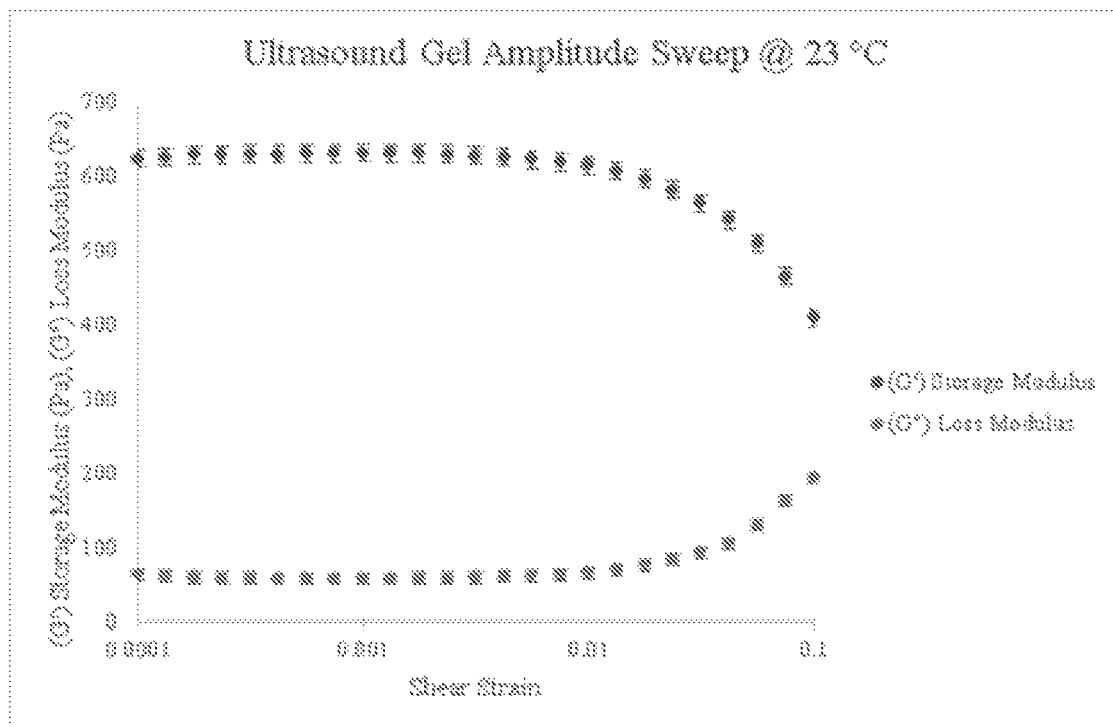
FIG. 2(a) is a graph of amplitude sweep data for a commercially available ultrasound coupling gel at 23° C.
Figure 2B:
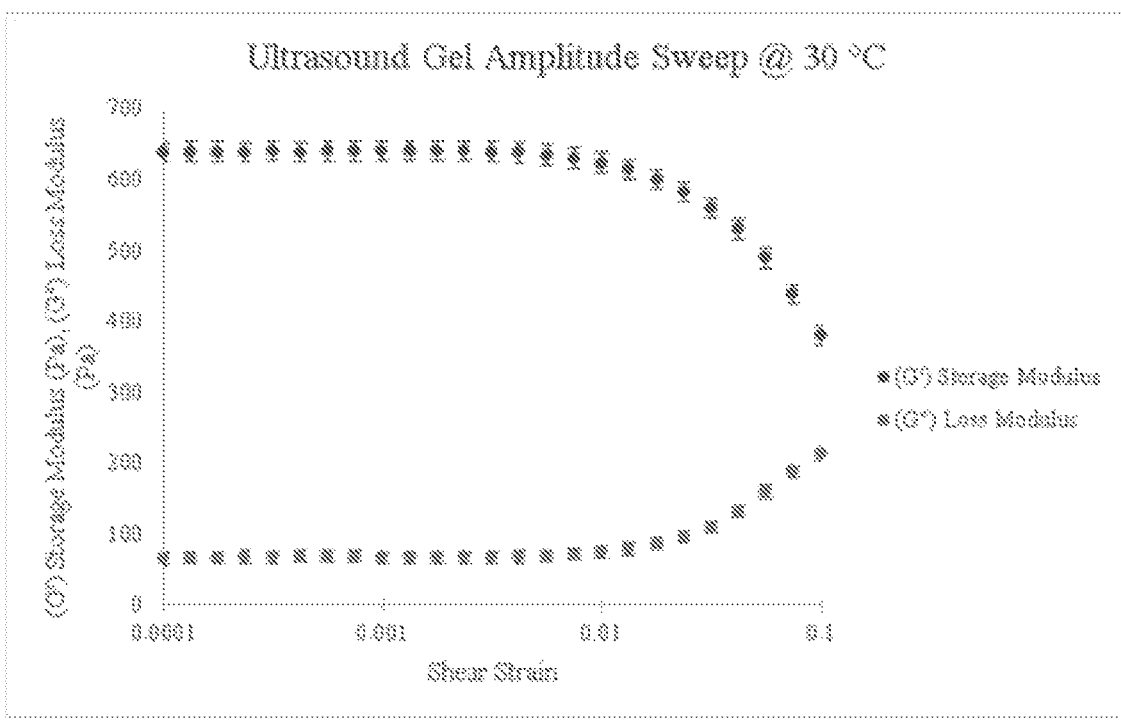
FIG. 2(b) is a graph of amplitude sweep data for a commercially available ultrasound coupling gel at 30° C.
Figure 2C:
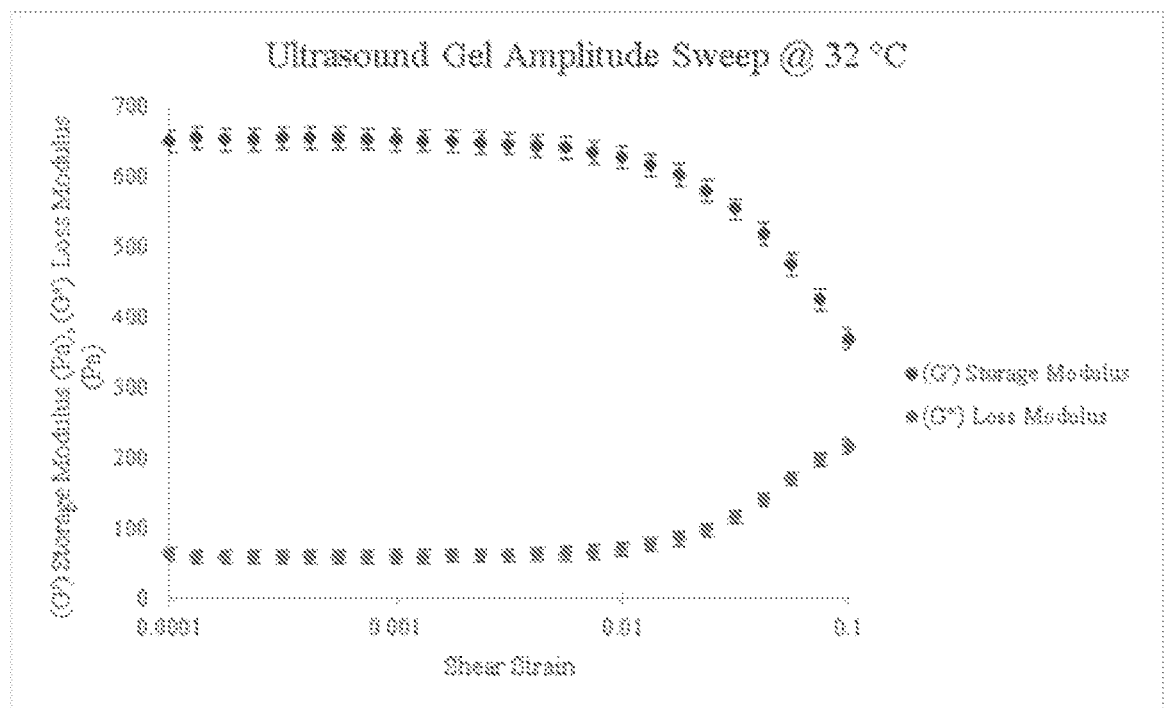
FIG. 2(c) is a graph of amplitude sweep data for a commercially available ultrasound coupling gel at 32° C.
Figure 2D:
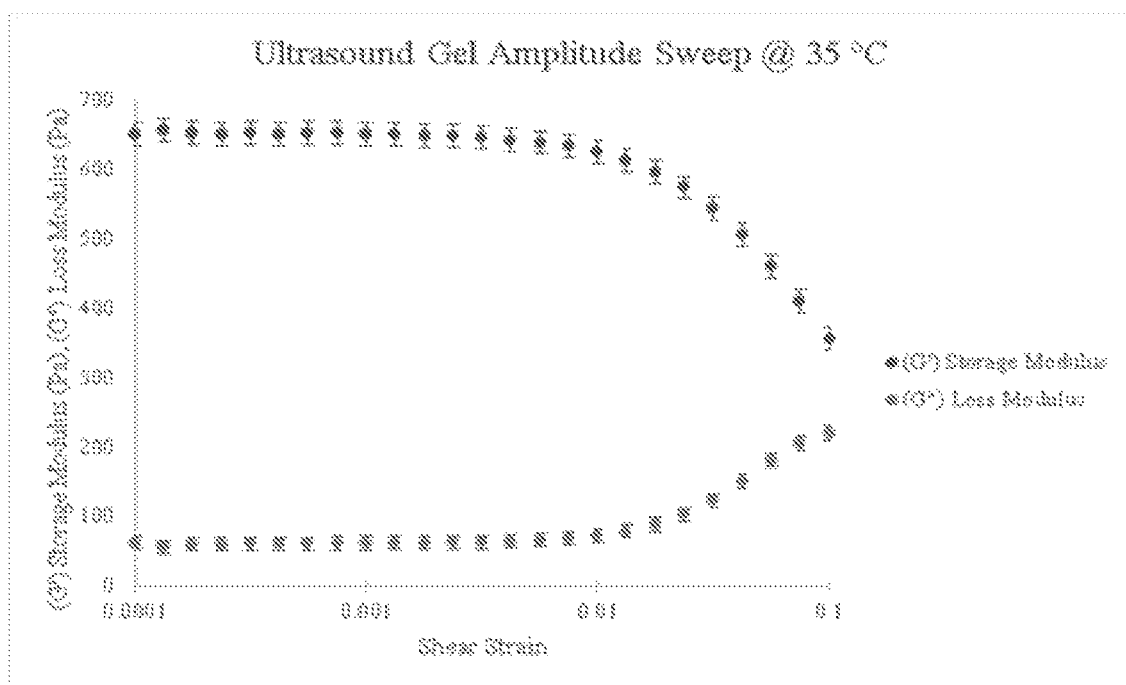
FIG. 2(d) is a graph of amplitude sweep data for a commercially available ultrasound coupling gel at 35° C.
Figure 2E:
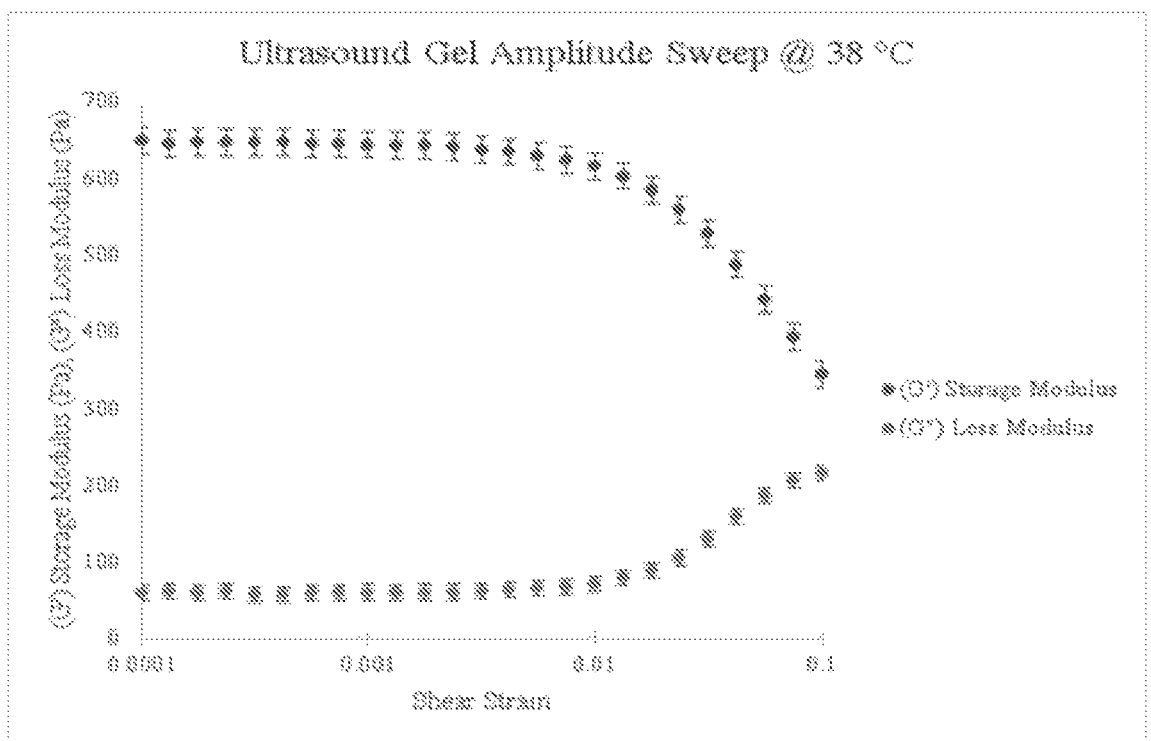
FIG. 2(e) is a graph of amplitude sweep data for a commercially available ultrasound coupling gel at 38° C.

The thermo-responsive ultrasound coupling gels and methods and uses of the present application are now described by reference to the embodiments. The description provided herein is not intended to limit the scope of the claims, but to exemplify the variety encompassed by the present application. Embodiments of the claims may, however, be embodied in many different forms and should not be construed as limited to the embodiments set forth herein.

The Thermo-Responsive Ultrasound Coupling Gel

The thermo-responsive ultrasound coupling gel contains a thermo-responsive polymer. Such thermo-responsive polymers are polymers that change properties when experience a change in temperature. Nonetheless, the thermo-responsive ultrasound coupling gel is generally a three-component solution that is configured to be a viscous coupling gel for ultrasound-guided procedures. For example, the procedures may include those that require ultrasound guided location of a patient's anatomy, but also stability of an ultrasound probe for a given duration when pressed against a patient. Thus, typical procedures may include nerve blocks, placing nerve block catheters, biopsy of the liver and kidneys, cannulation of arteries and veins, and the like. However, the thermo-responsive ultrasound coupling gel can also be used in standard ultrasound procedures, or even in industrial applications.

The coupling gel is further configured to become less viscous for a short duration (e.g., for approximately 1 to 2 minutes) upon heating. The heating can be provided by a microwave, but can also be provided from other sources, such as an infrared source, a chemical source, a mechanical source (e.g., friction) or the like. During the aforementioned short duration, the practitioner may scan the patient with little resistance to movement of the probe. After approximately two minutes, the viscosity and adhesiveness of the coupling gel increases significantly. Movement of the probe at this time is still possible, but requires more effort of the practitioner as compared to typical ultrasound gel. Thus, probe drift using the coupling gel is minimized generally relative to typical ultrasound gels when the actual needle based procedure is performed. That is, the thermo-responsive coupling gel behaves as an elastic solid with low tack at increased temperatures (e.g., ≥35° C.), wherein the gel is slippery and used for ultrasound scanning. As the gel cools to skin temperature (e.g., 32 to 34° C.), the gel becomes a viscoelastic liquid with increased tack, wherein drift is reduced thereby allowing the practitioner to accurately guide the needle tip to the target of interest.

The thermo-responsive ultrasound coupling gel can contain, as the three-component solution, a thermo-responsive polymer, a solvent, and a gelling agent. The thermo-responsive polymer can be selected from known thermo-responsive polymers, such as poly(n-isopropyl acrylamide) and poly(n-isopropyl methacrylamide). In particular, poly(n-isopropyl acrylamide) is a thermo-responsive polymer that undergoes physical crosslinking when exposed to a certain level of heat. The lowest critical solution temperature ("LCST") for poly(n-isopropyl acrylamide) is approximately 32° C. However, when in solution with polyvinyl alcohol and hydroxy (propylmethyl) cellulose, the temperature of activation is approximately in the range of 32 to 35° C. At this temperature threshold, the solution transitions from a semi-translucent state to a cloudy, white, and opaque state. Other thermo-responsive polymers that have similar properties may be utilized. The thermo-responsive polymer can be a single thermo-responsive polymer or a mixture of thermo-responsive polymers. In the thermo-responsive ultrasound coupling gel, the thermo-responsive polymer can be provided in a solution with water. The amount of thermo-responsive polymer in the solution can be 1-10% by weight relative to the weight of the solution. Alternatively, the amount of thermo-responsive polymer in the solution can be 2-8% by weight, 2-6% by weight, and/or 3-5% by weight, but is not particularly limited. In an embodiment, the amount of thermo-responsive polymer in the solution is 4% by weight.

The solvent can be selected from known solvents, such as water and alcohols. The solvents can be a single solvent or a mixture of solvents. For instance, the solvent can a mixture of water and polyvinyl alcohol. In the thermo-responsive ultrasound coupling gel, the solvent can be provided in a solution with water. The amount of solvent in the solution can be 10-30% by weight relative to the weight of the solution. Alternatively, the amount of solvent in the solution can be 15-25% by weight, 15-20% by weight, and/or 16-18% by weight, but is not particularly limited. In an embodiment, the amount of solvent in the solution is 17% by weight. The preparation of a polyvinyl alcohol solution can result in a viscous solution. Thus, even though the aforementioned components are described as solvents, the polyvinyl alcohol can also act to influence the properties of the thermo-responsive ultrasound coupling gel.

The gelling agent can be selected from known gelling agents, such as cellulose polymers, synthetic polymers, natural polymers, semi-synthetic polymers, and mixtures thereof. Examples of cellulose polymers include, but are not limited to, methyl cellulose, hydroxypropyl cellulose, hydroxy(propylmethyl) cellulose, and carboxy methyl cellulose. In an embodiment, the gelling agent is hydroxy (propylmethyl) cellulose. Examples of natural polymers include, but are not limited to, gelatin, casein, collagen, egg whites, polysaccharides like guar gum, acacia, tragacanth, bug bean gum, pectin, starch, xanthan gum, dextran, and succinoglucon. Examples of semi-synthetic polymers include, but are not limited to cellulose subordinates, magnesium aluminum silicate, methylcellulose, and sodium alginate. Examples of synthetic polymers include, but are not limited to, carbomers, poloxamers, and polyvinyl alcohol. In the thermo-responsive ultrasound coupling gel, the gelling agent can be provided in a solution with water. The amount of gelling agent in the solution can be 10-30% by weigh. Alternatively, the amount of gelling agent in the solution can be 15-25% by weight, 15-22% by weight, and/or 19-21% by weight, but is not particularly limited. In an embodiment, the amount of gelling agent in the solution is 20% by weight.

To prepare the thermo-responsive ultrasound coupling gel, a thermo-responsive polymer, a solvent, and a gelling agent can be mixed. Each of the thermo-responsive polymer, the solvent, and the gelling agent can be provided in one or more solutions or individually. For example, the thermo-responsive polymer can be provided in first solution, but the solvent and the gelling agent can be provided in a second solution. Nonetheless, each of the thermo-responsive polymer, the solvent, and the gelling agent are envisioned to be provided in separate solutions. In this regard, since each of the thermo-responsive polymer, solvent, and gelling agent can be prepared in a solution with water, the respective solutions can be mixed to prepare the thermo-responsive ultrasound coupling gel. In an embodiment, the solutions of the thermo-responsive polymer, solvent, and gelling agent are mixed in equal amounts by weight in a 1:1:1 ratio. In another embodiment, the solutions of the thermo-responsive, solvent, and gelling agent can be mixed in 4-1:1:1, 1:4-1:1, and/or 1:1:4-1 ratios. The solutions of the thermo-responsive, solvent, and gelling agent can be mixed in 3-1:1:1, 1:3-1:1, and/or 1:1:3-1 ratios, as well as 2-1:1:1, 1:2-1:1, and/or 1:1:2-1 ratios. The ratios can be adjusted, for example, so that the tack can be adjusted without substantially affecting temperature dependence. For instance, the thermo-responsive ultrasound coupling gel has a tack at ≤32° C. that is ≥20% of a tack at ≥35° C. The thermo-responsive ultrasound coupling gel may also have a tack at ≤32° C. that is ≥30%, 50%, and/or 100% of a tack at ≥35° C. The tack can also be adjusted by selecting the components.

In addition to the above-mentioned components, the thermo-responsive ultrasound coupling gel can contain additional components, such as diluting agents, preservatives, antioxidants, fragrances, humectants, oils, emulsifiers, colorants, thickeners, stabilizers, binders, texturizers, pH control agents, and mixtures thereof.

The thermo-responsive ultrasound coupling gel can be characterized by at least considering the storage modulus (G'), the loss modulus (G"), and loss factor (G"/G') of the thermo-responsive ultrasound coupling gel. The storage modulus (G') is a representation of the elastic properties of the viscoelastic behavior of a material. The loss modulus (G") is a representation of the viscous properties of the viscoelastic behavior of a material. The loss factor (G"/G') is a ratio of the loss and storage modulus of a material used to describe the material's viscoelastic properties. An elastic solid is a material state in which the storage modulus is larger than the loss modulus (G'>G"), and this phase state occurs when the force applied to the material is smaller than that of the intermolecular forces. As a result, the material possesses a capacity to store energy and the ability to return to its initial configuration to an extent upon the removal of the force. In this state, the elastic properties of the system are dominant. A viscoelastic liquid is a material state in which the loss modulus is larger than the storage modulus (G">G'), and this phase state can occur if the force applied to a material is larger than that of the intermolecular forces. As a result, the microstructure of the material collapses and the mechanical energy transferred to the material dissipates, allowing the material to flow. In this state, the material becomes a viscous dominant system.

The thermo-responsive polymer acts as a viscoelastic liquid at temperatures below its LCST and possesses a high level of adhesive performance. The LCST is the temperature at which the thermo-responsive polymer begins to exhibit lower liquid miscibility as compared to its unreacted state. As a result, the LCST is often a transition temperature for the phase state of a substance. In an embodiment where the thermo-responsive polymer is poly(n-isopropyl acrylamide), the LCST is approximately 32° C. Once the is poly(n-isopropyl acrylamide) is heated past its LCST to a temperature of 35° C., the gel undergoes physical crosslinking leading to a phase transition to an elastic solid state in which the adhesive properties are lowered. That is, the thermo-responsive ultrasound coupling gel has a phase shift at a temperature in the range of 32 to 35° C. such that the gel has a loss factor G"/G' of >1 at <32° C. and a loss factor G"/G' of <1 at >35° C. The phase transition allows for the gel to be spread onto the skin of a patient with ease and control. As the gel cools from its initial heated temperature, its adhesive performance returns to nearly its full original capacity, allowing the ultrasound probe to stabilize over the located target tissue within 1 to 2 minutes after the initial heat application. As a result of the controlled phase state changes, the gel is able to provide desirable scanning conditions for 1 to 2 minutes after the initial heating process and decrease drift during the procedure in a manner that commonly used ultrasound gels cannot.

Even though the thermo-responsive polymer gel has temperature dependent properties, the variation of these properties does not affect ultrasound imaging. For instance, the gel can have a cloudy appearance or a clear appearance, but the appearance does not affect the ultrasound imaging. The thermo-responsive polymer gel properties (e.g., tack, viscosity) are also substantially unaffected by pressure, such as when the ultrasound probe is pressed on patient to compress tissue to identify nerve.

Sterilization

The thermo-responsive ultrasound coupling gel can be sterilized by known sterilization methods. In an embodiment, the thermo-responsive ultrasound coupling gel is sterilized by subjecting the thermo-responsive ultrasound coupling gel ultraviolet light. However, the thermo-responsive ultrasound coupling gel can also be sterilized prior to packaging.

Method of Application and Uses

The method for applying the thermo-responsive ultrasound coupling gel can include heating the thermo-responsive ultrasound coupling gel to a temperature≥35° C. and then applying the thermo-responsive ultrasound coupling gel to a patient. As discussed above, the thermo-responsive ultrasound coupling gel experiences a phase shift in a temperature range of 32 to 35° C. Thus, by heating the thermo-responsive ultrasound coupling gel to a temperature≥35° C., the thermo-responsive ultrasound coupling gel has a loss factor G"/G' of <1. That is, the thermo-responsive ultrasound coupling gel has an elastic solid state in which the adhesive properties are lowered, which allows for the gel to be spread onto the skin of a patient with ease and control. The heating can be performed by, for example, heating the thermo-responsive ultrasound coupling gel in a microwave, but can also include heating via infrared source, a chemical source, a mechanical source (e.g., friction) or the like. Also, the thermo-responsive ultrasound coupling gel can be heated in a temperature controlled liquid bath.

The thermo-responsive ultrasound coupling gel can be applied to the patient at a temperature≥35 and/or ≤38° C. After the application to the patient, the thermo-responsive ultrasound coupling gel is allowed to cool to a temperature<35° C., <32° C., or in a temperature in the range of 32 to 35° C. The cooling can be performed by simply allowing the gel to naturally cool to room temperature or skin temperature, but can also be assisted by cooling devices, such as fans or blowing. Typically, the cooling takes 1 to 2 minutes. During this time, the practitioner can take advantage of the slipperier nature of the gel to position the ultrasound probe. However, by cooling the gel to a temperature<35° C., a phase shift occurs such that the loss factor G"/G' becomes >1. In such a phase, the gel becomes viscous, allowing the ultrasound probe to experience reduced drift. Once the gel becomes viscous, an ultrasound guided procedure, such as nerve blocks, nerve block catheters, biopsy of the liver and kidneys, cannulation of all arteries and veins, etc., can more efficaciously occur due to the reduced drift and tack.

EXAMPLES

Objects and advantages of this disclosure are further illustrated by the following examples, but the particular materials and amounts thereof recited in these examples, as well as other conditions and details, should not be construed to unduly limit this disclosure.

Embodiments of the thermo-responsive ultrasound coupling gel was prepared utilizing the following components and methods.

Polyvinyl alcohol ("PVA") obtained from Sigma Aldrich (No. 363146: molecular weight 85,000-124,000 Daltons; viscosity of 28-32 cP) was combined with distilled water at 80° C., thereby creating a PVA solution that was 17% by weight using a hot stir plate. During the stirring process, additional distilled water was added to the mixture periodically to compensate for evaporation in the amount of 30% of the total mixture weight. The stirring process took approximately 1 hour and 15 minutes. The PVA solution was then left to cool to room temperature after the PVA had fully dissolved. While not wishing to be bound by a single theory, the PVA acted at least as a partial solvent for the overall thermo-responsive ultrasound coupling gel.

Hydroxy(propylmethyl) cellulose ("HPMC") obtained from Sigma Aldrich (No. H9262: molecular weight of approximately 26,000 daltons; average viscosity of 80-120 cP) was combined with distilled water at room temperature creating a 20% solution by weight. The mixture was stirred by hand due to its high viscosity until the HPMC was completely dissolved. Mixing by hand stirring took approximately 10 to 12 minutes. While not wishing to be bound by a single theory, the HPMC was included within the formulation as the chief viscosity control of the thermo-responsive ultrasound coupling gel.

Poly(n-isopropyl acrylamide) ("PNIPA") obtained from Scientific Polymer Products Inc. (No. 963: molecular weight of 300,000 Daltons; inherent viscosity of 1 dL/g) was combined with distilled water at room temperature, thereby creating a 4% solution by weight. The mixture was vortexed in a 50 mL conical for a short time, and then left to set until all of the solid PNIPA particles completely dissolved. While not wishing to be bound by a single theory, the PNIPA is believed to be responsible for the thermoresponsive reaction that triggers the shift in the physical properties of the thermo-responsive ultrasound coupling gel from a viscoelastic liquid to an elastic solid.

The three solutions discussed above (i.e., PVA, HPMC, and PNIPA) were combined in equal parts after being prepared as discussed above, and stirred by hand until the resulting solution was homogeneous and uniform, which took approximately 10 to 12 minutes of stirring. The resulting embodiment of the thermo-responsive ultrasound coupling gel is hereinafter referring to as "magic gel."

As seen in FIGS. 1(a) and (b), the solution comprised of a 17% PVA solution, a 20% HPMC solution, and a 4% PNIPA solution is shown in its non-reacted state prior to heat exposure in FIG. 1(a), and immediately after heat exposure in FIG. 1(b). In FIG. 1(a), the solution has a slightly cloudy appearance while maintaining some transparency, whereas, in FIG. 1(b), the solution is not transparent and completely cloudy.

Sterilization

The magic gel was stored in 2 mL packets made of an aluminum oxide coated polyester to prevent any leeching of molecules or chemicals, either into or out of the packet/gel. The packet also prevented evaporation of the solution and ensured solution sterility was maintained. Ten packets were exposed to a 365 nm ultraviolet light with a 360 watt source for 30 seconds each. The contents of the ten packets were then placed onto blood auger plates and incubated at room temperature for seven days. Each of the ten packets showed no signs of bacteria or foreign contaminates after the incubation period, indicating that the gel can be sterilized through a simple application of ultraviolet light after the gel has already been packaged.

Rheometer Test Data

The magic gel was subjected to a series of tests with the use of a rheometer in order to demonstrate the controllable variation in performance of the magic related to temperature and strain at various levels as compared to that of the uniformly performing standard ultrasound gel. Using a rheometer, the magic gel and a standard commercially available ultrasound gel were placed through a series of tests to compare the properties of the magic gel and the standard commercially available ultrasound gel. The standard commercially available ultrasound gel used was AQUA-SONIC® 100 manufactured by Parker Laboratories, Inc.

To describe the way in which the two gels responded to various temperatures and shear strains, both gels were subjected to amplitude sweeps. The amplitude sweeps were conducted to describe the deformation and dispersion behavior of a gel. An Anton Paar MCR 302 Rheometer with 50 mm diameter, 1° steel cone probe attachment was used.

The amplitude sweeps were conducted at a constant and even frequency of 1 Hz, in addition to a set shear strain rate interval of 0.01%-10%. The sweeps were conducted at five different temperatures: 23° C., 30° C., 32° C., 35° C., and 38° C. The temperatures were selected based on the 32° C.

LCST of the thermo-responsive PNIPA. In order to observe the full phase-shift spectrum of the magic gel in both its unreacted and reacted states, two temperatures were selected on both sides of the LCST in addition to the LCST itself for testing.

Ten samples of each gel were tested at each temperature. The amplitude sweeps were able to provide information on the storage modulus (G'), loss modulus (G"), and loss factor (G"/G'). Each of the storage modulus (G'), loss modulus (G"), and loss factor (G"/G') can be used to describe the linear viscoelastic performance of the magic gel as compared to that of standard ultrasound gel as well as any potential shifts between an elastic solid and a viscoelastic liquid phase state. The data for each of the ten tests at each temperature for each gel was averaged and analyzed. The storage modulus and loss modulus were plotted against the shear strain at each temperature for both the magic gel and the standard ultrasound gel to observe any significant changes in the phase state of the material. A cone probe attachment was used specifically because the geometry of the attachment coupled with the contact surface of the gel allowed for a uniform shear environment across the entire area of the tested gel sample. This allowed for the entire sample being tested to experience a uniform shear strain in a manner that yields consistent and accurate moduli data results.

The analysis of the storage modulus (G') and loss modulus (G") provide a specific insight into the viscoelastic behavior of the magic gel and standard ultrasound gel as it relate to temperature. Such behavior can also be characterized through the loss factor. The loss factor is the ratio of the loss modulus to the storage modulus (G"/G'). When a material is a viscous dominant system (G">G') the numerator is larger than the denominator, causing the ratio to be greater than 1. When a material possesses greater elastic solid properties (G"<G'), the denominator is larger than the numerator, causing the ratio to be less than 1. Therefore, if the material behaves as a viscoelastic liquid, the loss factor is greater than 1, and, if the material behaves as an elastic solid, the loss factor is less than 1. Using the information provided by the amplitude sweeps, the loss factor for the magic gel and standard ultrasound gel were averaged at each temperature for each gel, and then plotted against the shear strain in order to depict a more simplistic representation of the aforementioned moduli data.

Another component in both describing and understanding the nature of the flow of a substance is the tack, which characterizes the adhesive performance of a material. The tack of the magic gel pertains to both the comparison to the standard ultrasound gel as well as to itself from its unreacted state to its reacted state on both sides of the LCST. An object for the magic gel was to exhibit a greater adhesive performance than that of standard ultrasound gel, but with a controllable variability based upon the application of heat as the phase of the gel was effectively manipulated.

A tack test was also conducted with the use of a rheometer in order to describe the comparative differences between the adhesive performance of the magic gel and the standard ultrasound gel. The negative normal force registered by the upward movement of the rheometer probe from the starting position of the probe at the point of contact with the sample, to its final stopped position above the material is a relative measure of tack of the material. Therefore, the larger the negative normal force registered through a tack test, the greater the adhesive performance of the material. This information aids the understanding of the performance of the magic gel since it relates to the phase shift the magic gel experiences with exposure to various temperatures. For this test, a 25 mm parallel plate rheometer probe was used as the attachment. As with the amplitude sweeps, the tack tests were conducted at five different temperatures: 23° C., 30° C., 32° C., 35° C., and 38° C. Ten samples of each gel were tested at each temperature. The data was then averaged at each temperature for both gels. The negative normal force for both gels was then plotted against the respective gap distance between the probe attachment and the material, which is the distance the negative normal force is measured across during the test. This was done for each of the five tested temperatures.

In order to observer the empirical differences in adhesive performance between the magic gel in its unreacted and reacted states, tack tests for the magic gel were conducted and compared at both 23° C. and 35° C. The tack for 10 unreacted magic gel samples at 23° C. and 10 reacted magic gel samples at 35° C. was measured and recorded. The results for the 10 samples were then averaged together for each tested temperature in regard to both normal force and gap distance. The averaged normal force for each tested temperature was then plotted against the respective averaged gap distances associated with the normal force measurements. Of the averaged normal force data, the two largest normal force values were then averaged together for each temperature to obtain an average highest normal force for the unreacted gel at 23° C. and the reacted gel at 35° C. The average highest normal force for the unreacted and reacted samples were then compared against each other to obtain a percent difference in the adhesive performance experienced by the magic gel in its unreacted and reacted states. The same procedure was followed to obtain the percent difference in adhesive performance between standard ultrasound gel at 23° C. and 35° C. The percent difference in adhesive performance between the tested magic gel results was then compared against the percent difference of the tested standard ultrasound gel results.

To demonstrate the magic gel's ability to reduce its adhesive performance for the gel application process and then increase its adhesive performance to its original value on a hysteretic cycle, the magic gel was subjected to another set of tack tests with the use of the rheometer. For this series of tests however, the gel was first heated from 23° C. to 35° C., where the temperature remained for one minute. After the one-minute time period, the gel was then cooled back down to 23° C., where the temperature remained for another minute. The tack test was then performed immediately at the end of the second minute at 23° C. This was done for 10 separate trials, after which the results were averaged and graphed accordingly. Of the averaged normal force portion of the data, the two largest normal force values were averaged together to determine an average highest normal force for the magic gel on a hysteretic cycle. The same procedure was followed for the standard ultrasound gel to draw a comparison between the percent differences in adhesive performance between the two gels.

Removal Process

The process and ease with which the magic gel is removed from a potential patient was compared against the process and ease with which standard ultrasound gel is removed. In order to effectively compare the two, ten samples of each gel were separately applied to a standard ultrasound phantom in the amount of 2 mL each. The magic gel was heated to 35° C. and applied to the phantom, after which it was allowed to set for two minutes before being removed with water and a paper towel. The standard ultrasound gel was applied and then also removed with water and a paper towel. The number of wipes needed to remove the gel from the phantom using the damp paper towel was then recorded for each gel.

Results of Testing

The amplitude sweep data provided insight into the viscoelastic properties of both the magic gel and standard ultrasound gel. Through this data, it is possible to demonstrate how the elastic and viscous portions of the polymer change in accordance with the performance of each material. The standard ultrasound gel exhibited a constant elastic solid behavior across all temperature ranges as the storage modulus was larger than the loss modulus at each of the five temperatures. As FIGS. 2(a) to (e) show, the standard ultrasound gel performed as an elastic solid at each temperature indicating that there is little to no change in the viscoelastic properties of the gel as a result of either varying temperature or shear strain.

Figure 3A:
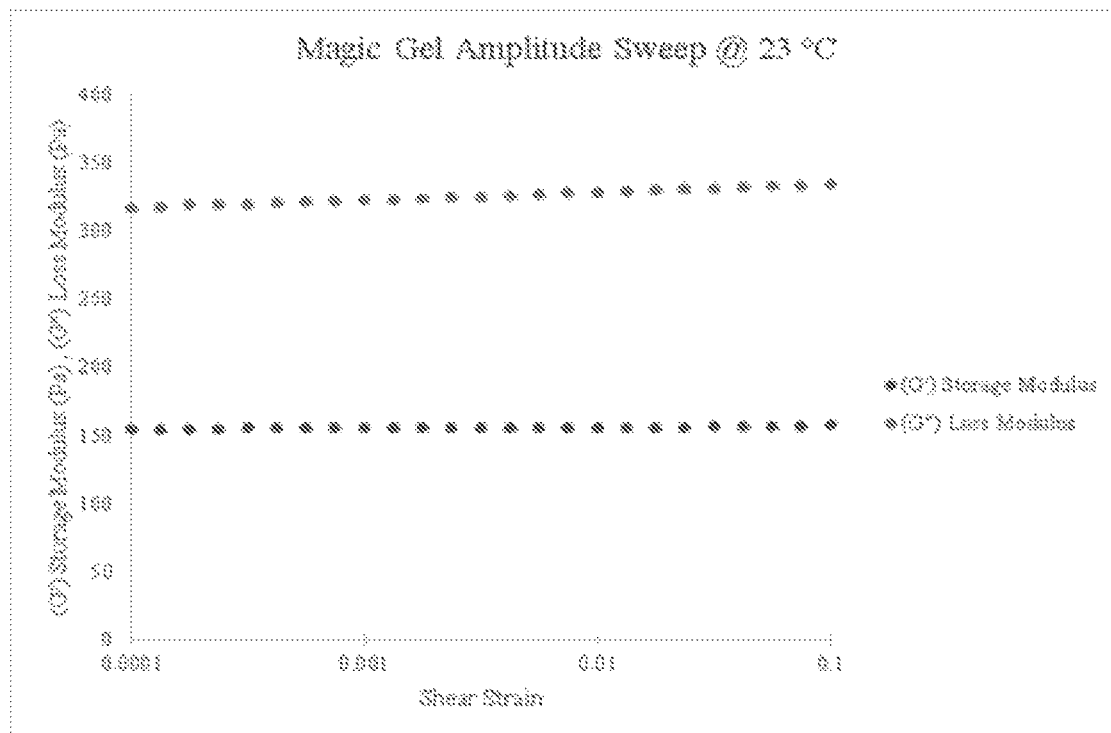
FIG. 3(a) is a graph of amplitude sweep data for an embodiment of the thermo-responsive ultrasound coupling gel at 23° C.
Figure 3B:
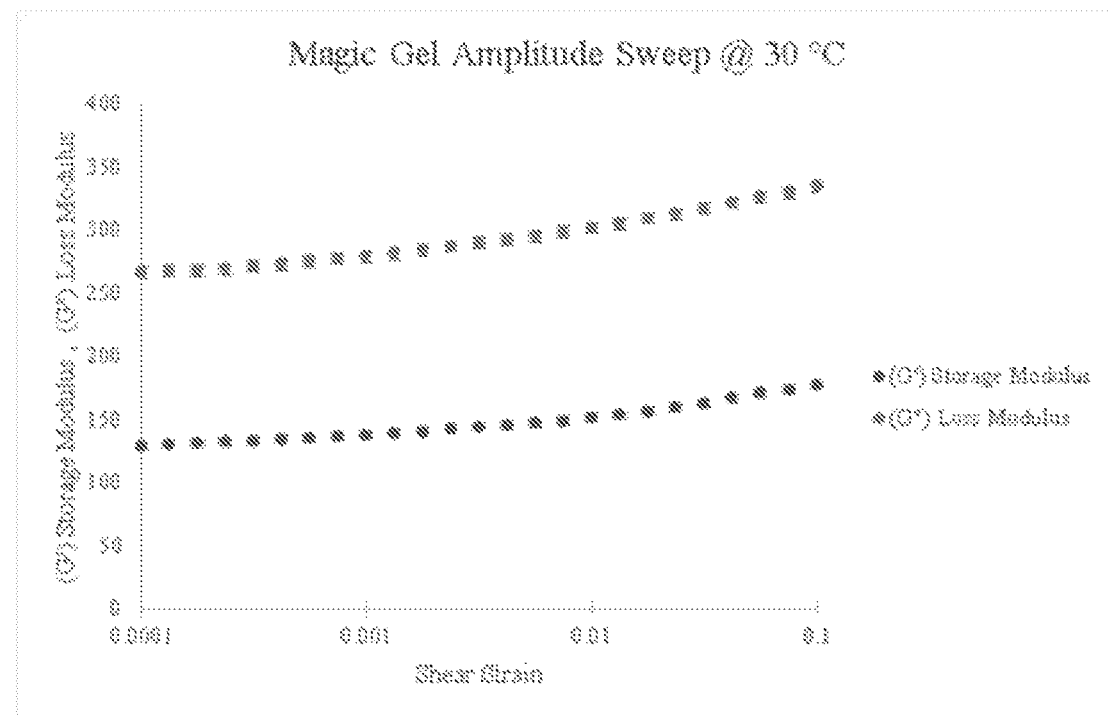
FIG. 3(b) is a graph of amplitude sweep data for an embodiment of the thermo-responsive ultrasound coupling gel at 30° C.
Figure 3C:
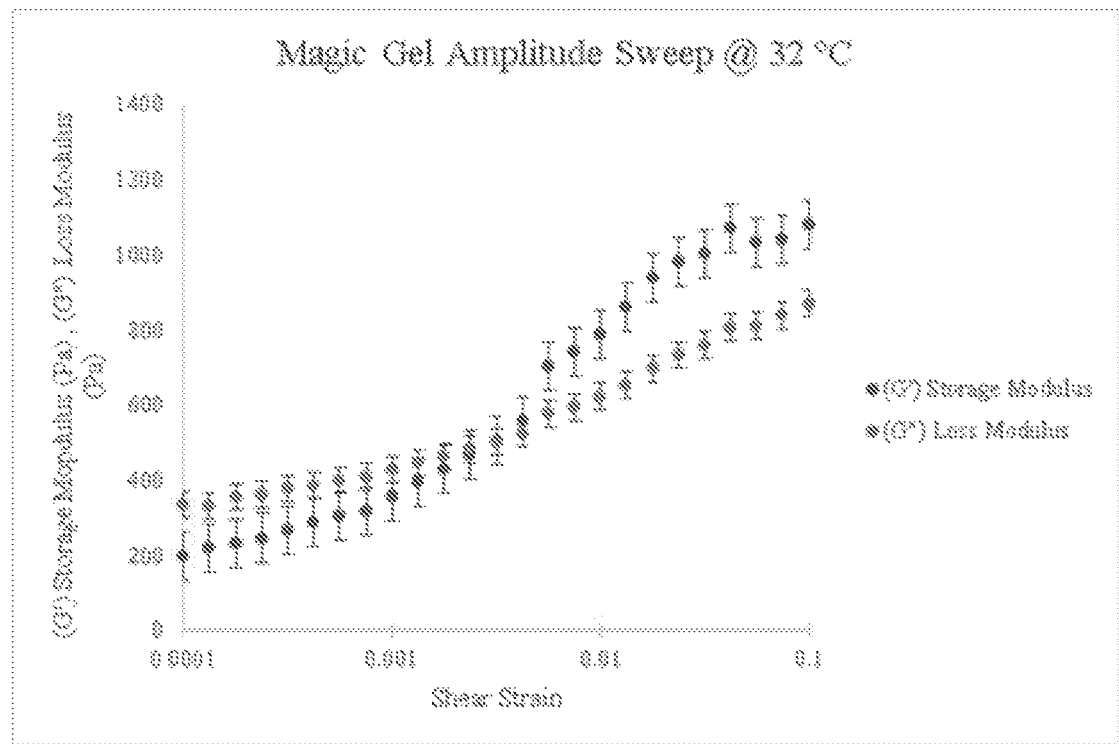
FIG. 3(c) is a graph of amplitude sweep data for an embodiment of the thermo-responsive ultrasound coupling gel at 32° C.
Figure 3D:
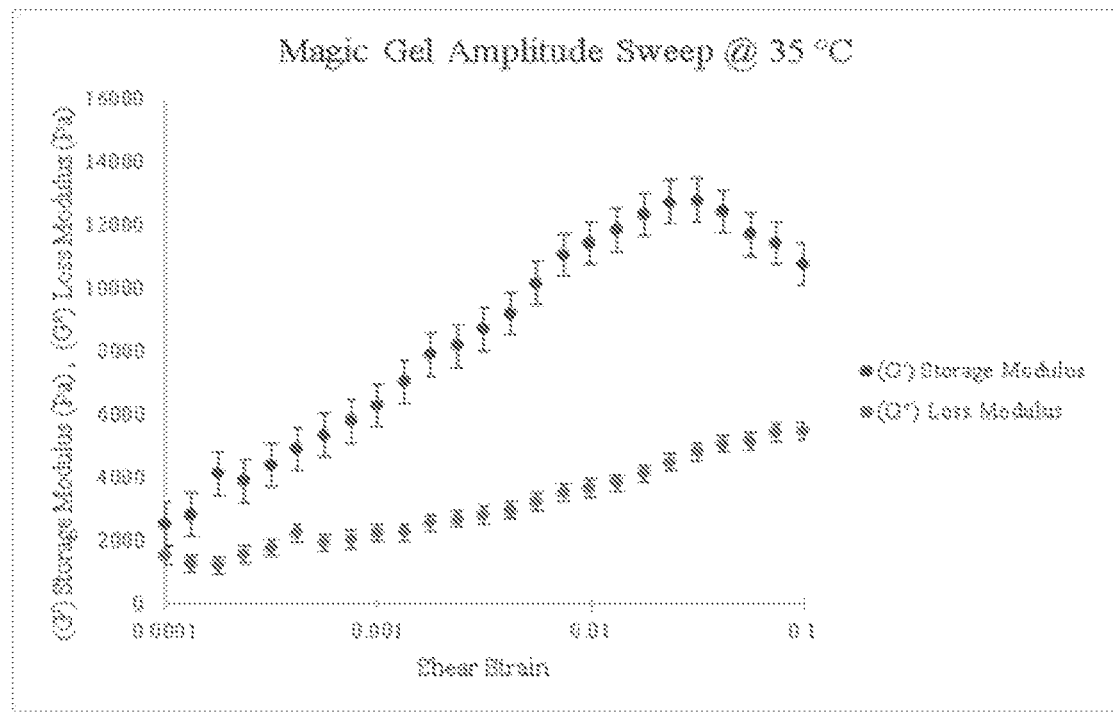
FIG. 3(d) is a graph of amplitude sweep data for an embodiment of the thermo-responsive ultrasound coupling gel at 35° C.
Figure 3E:
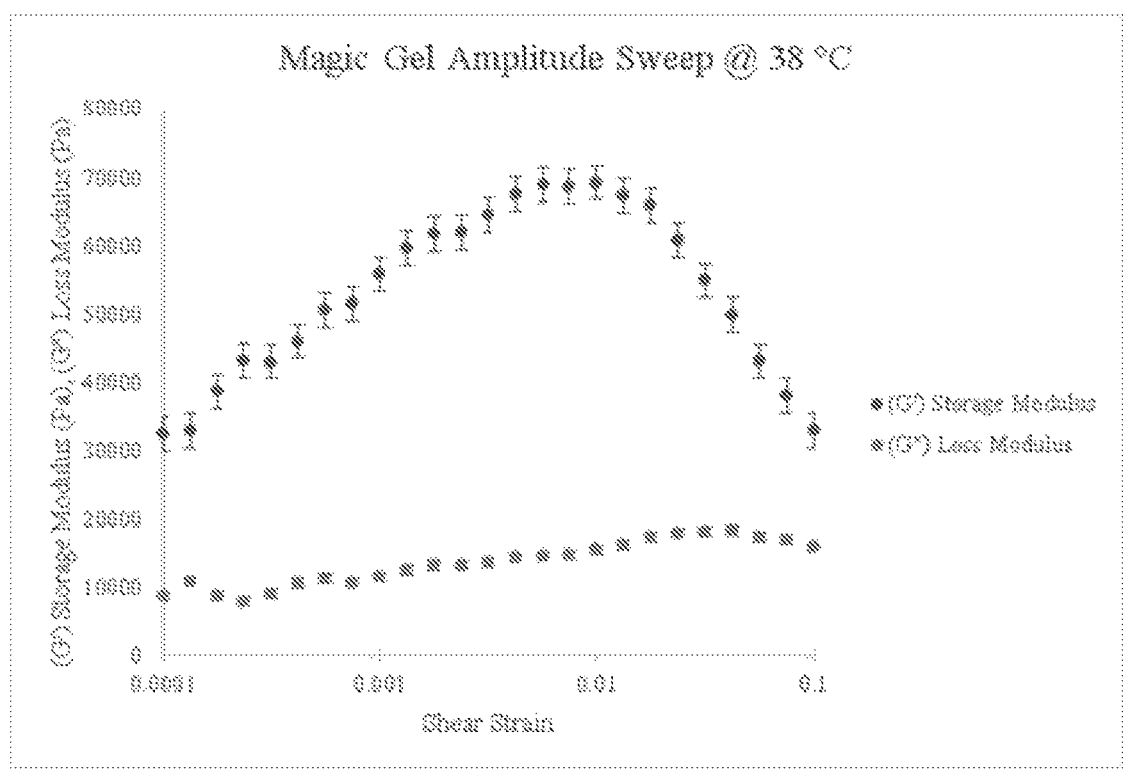
FIG. 3(e) is a graph of amplitude sweep data for an embodiment of the thermo-responsive ultrasound coupling gel at 38° C.
Figure 4A:
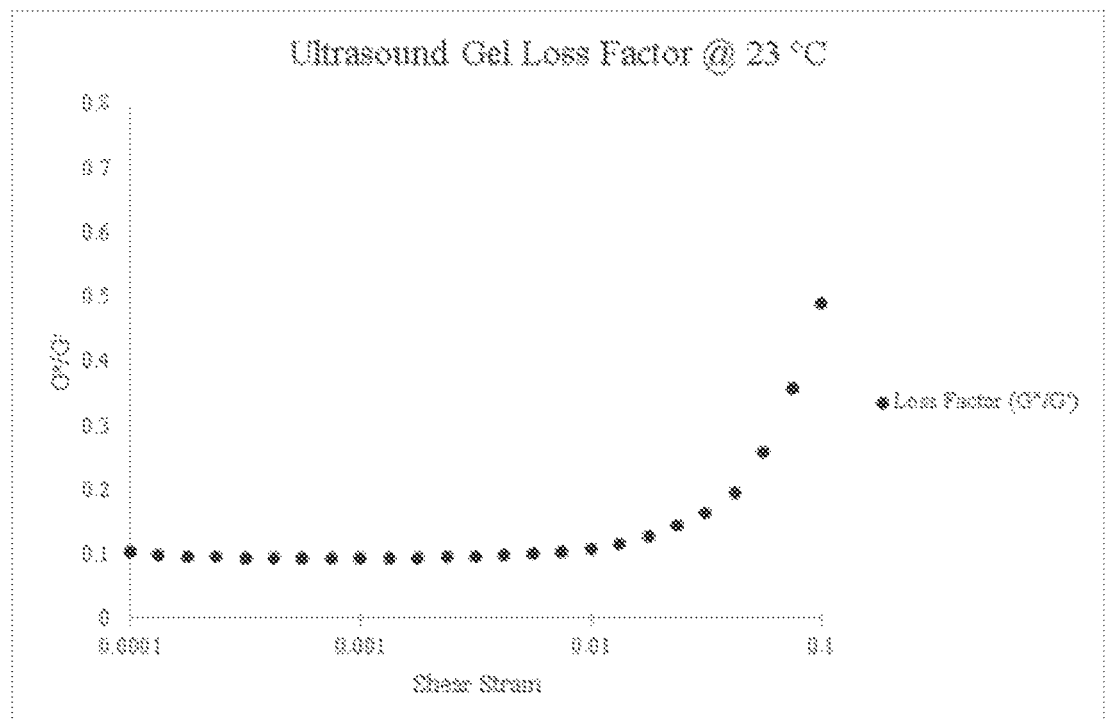
FIG. 4(a) is a graph of the loss factor for a commercially available ultrasound coupling gel at 23° C.
Figure 4B:
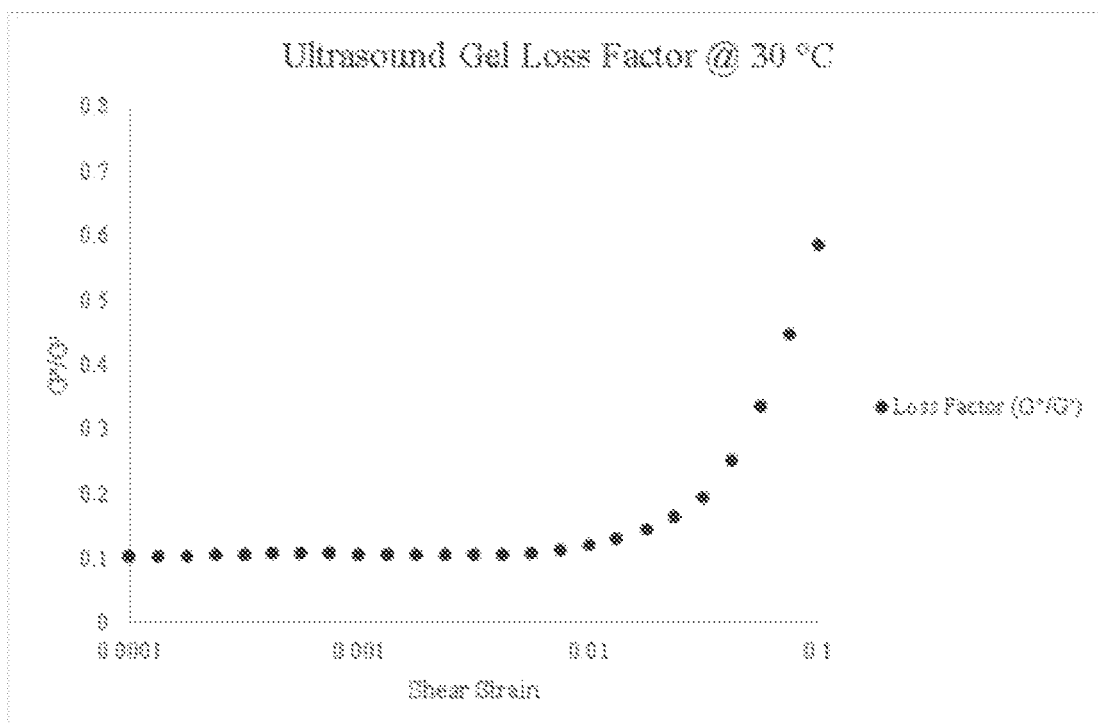
FIG. 4(b) is a graph of the loss factor for a commercially available ultrasound coupling gel at 30° C.
Figure 4C:
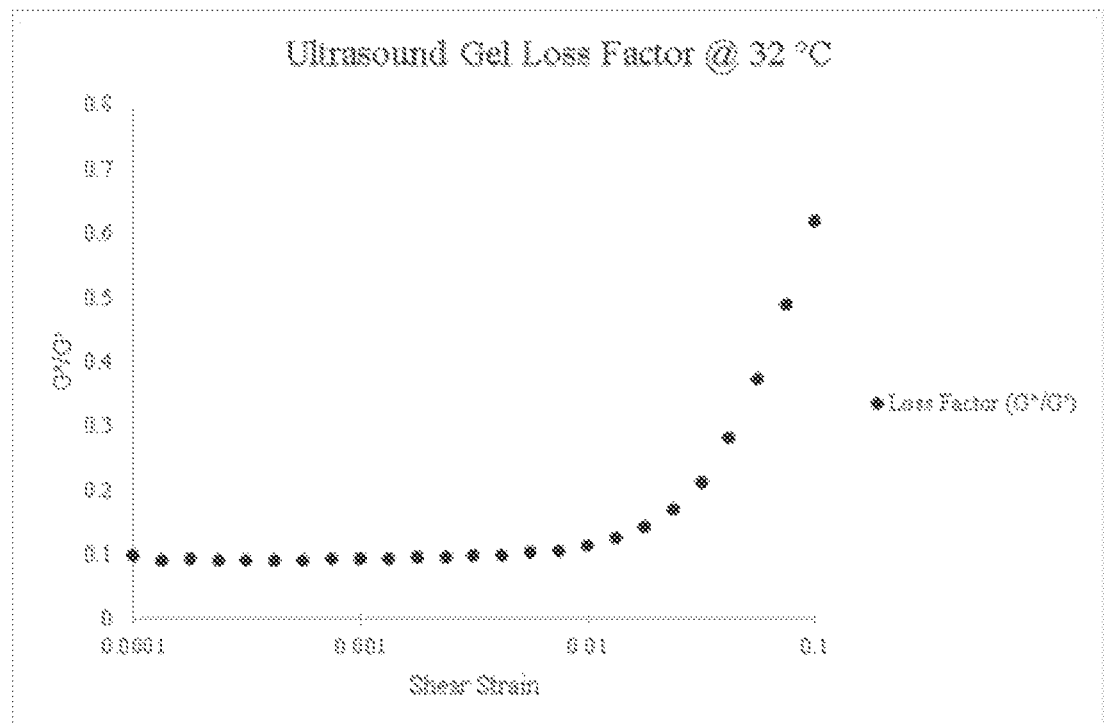
FIG. 4(c) is a graph of the loss factor for a commercially available ultrasound coupling gel at 32° C.
Figure 4D:
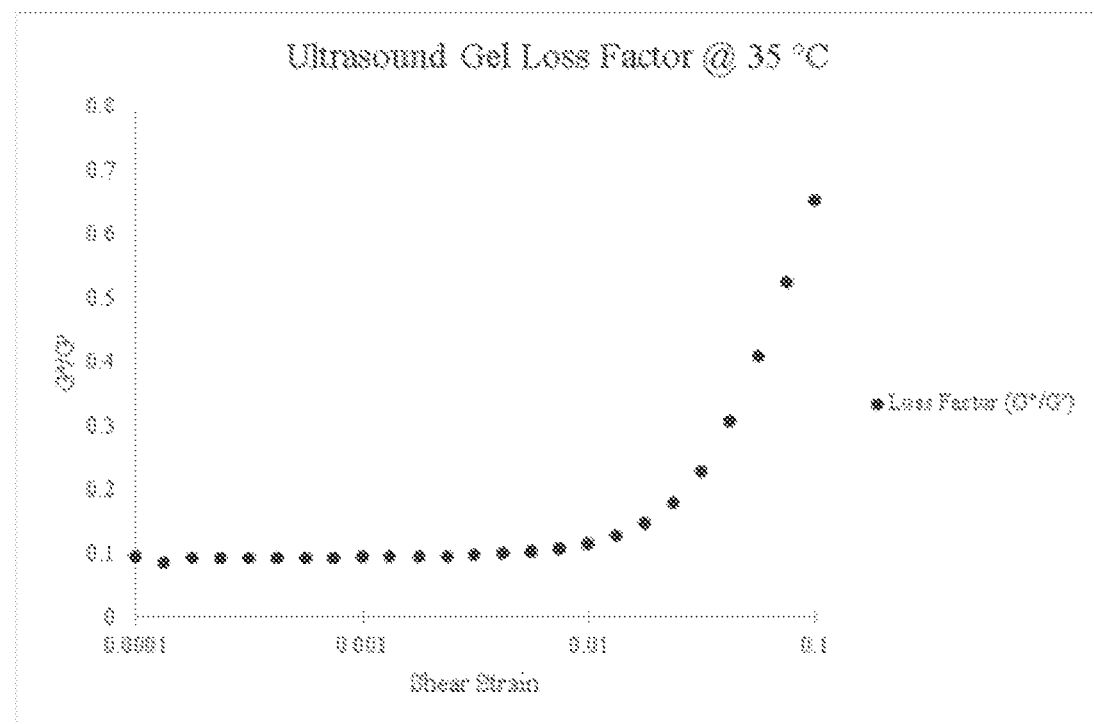
FIG. 4(d) is a graph of the loss factor for a commercially available ultrasound coupling gel at 35° C.
Figure 4E:
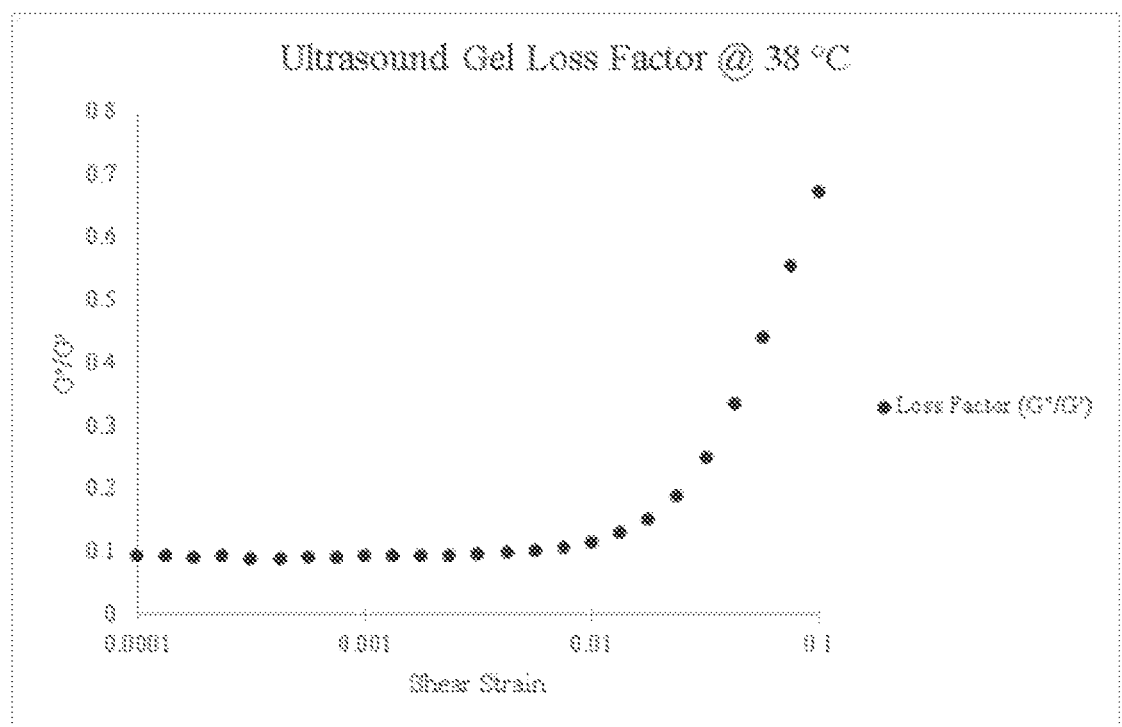
FIG. 4(e) is a graph of the loss factor for a commercially available ultrasound coupling gel at 38° C.

The magic gel performed in a manner very different from that of standard ultrasound gel, displaying varying viscoelastic properties with the increasing temperatures. As the graphs in FIGS. 3(a) to (e) demonstrate, the magic gel undergoes a significant phase shift as a result of the increasing temperature ranges. FIGS. 3(a) and 3(b) display the viscous behavior of the magic gel below the LCST at 23° C. and 30° C. FIG. 3(c) demonstrates the phase shift that the magic gel experiences as a result of eclipsing the LCST. At a temperature of 32° C., the gel can be seen transitioning from a viscoelastic liquid with a viscous dominant system to an elastic solid phase state. It is at this point that the moduli switch and the storage modulus becomes greater than the loss modulus. As the temperature increases to 35° C. and 38° C., the magic gel remains in the elastic solid state, displaying even greater elastic solid behavior. These results indicate that the magic gel possesses the ability to effectively transition from a viscoelastic liquid state to an elastic solid state with the application of heat, specifically at and above that of 32° C.

The loss factor graphs help to demonstrate what type, if any, of phase shift takes place within the tested sample in a more simplistic and general manner as compared to the raw storage and loss moduli data. As the graphs of FIGS. 4(a) to (e) show, the loss factor for the standard ultrasound gel at each of the tested temperatures is less than 1, supporting the previous observation that the ultrasound gel is a purely elastic solid material and does not possess the ability to transition between phases in any manner or perform any differently under other conditions.

Figure 5A:
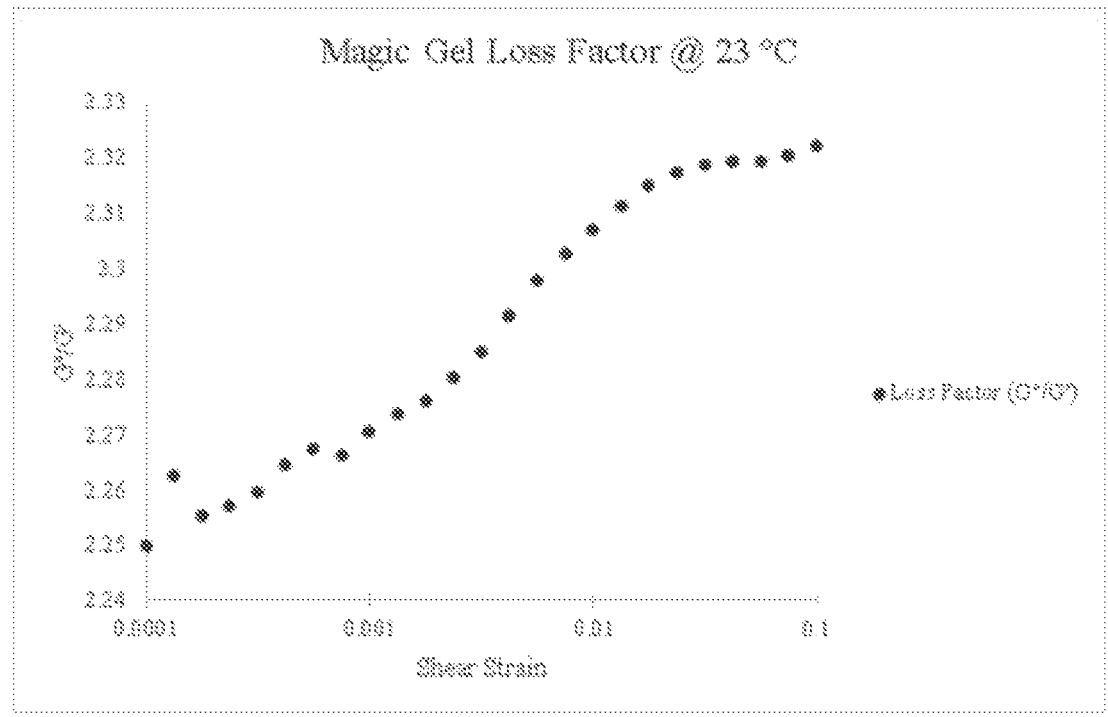
FIG. 5(a) is a graph of the loss factor for an embodiment of the thermo-responsive ultrasound coupling gel at 23° C.
Figure 5B:
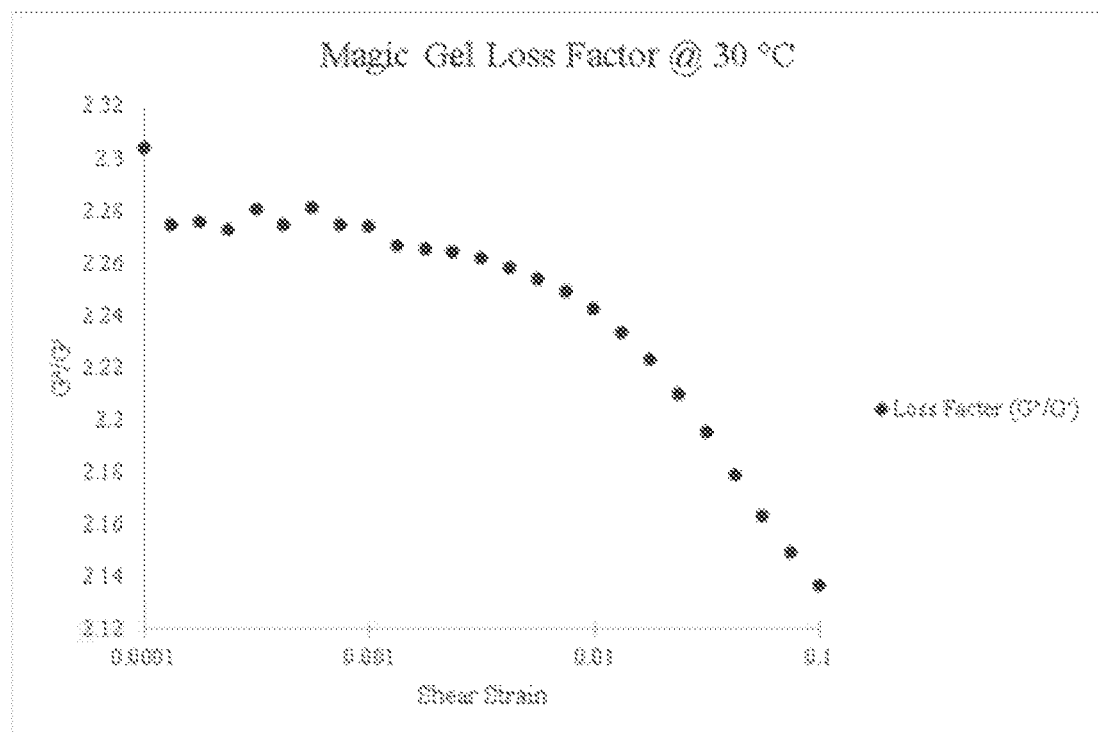
FIG. 5(b) is a graph of the loss factor for an embodiment of the thermo-responsive ultrasound coupling gel at 30° C.
Figure 5C:
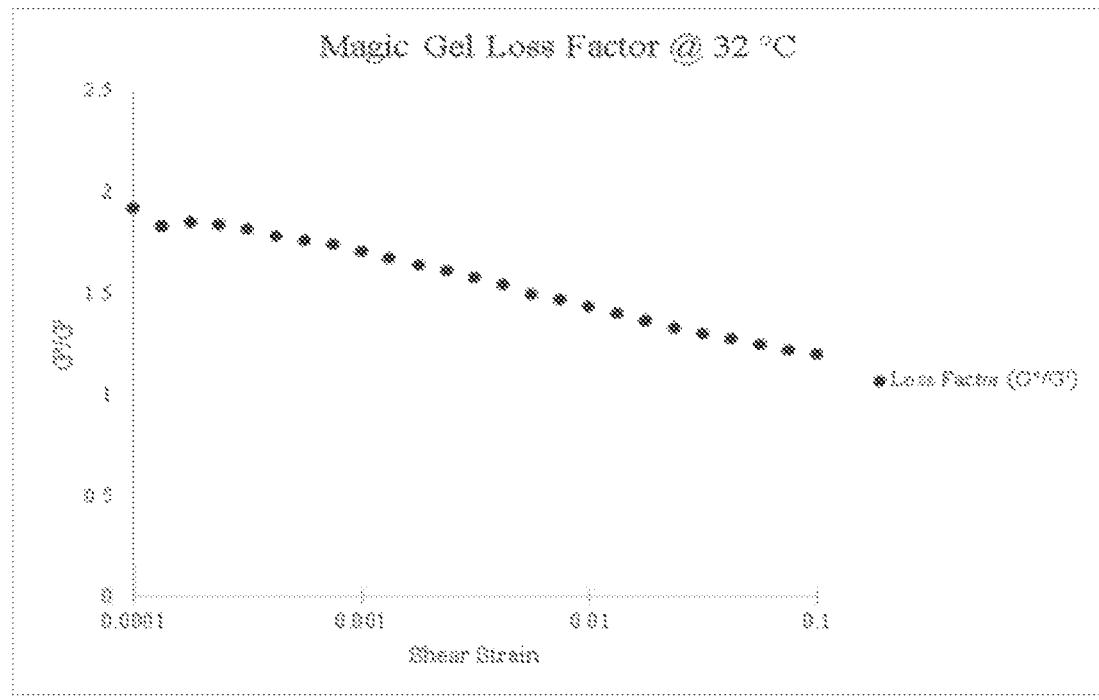
FIG. 5(c) is a graph of the loss factor for an embodiment of the thermo-responsive ultrasound coupling gel at 32° C.
Figure 5D:
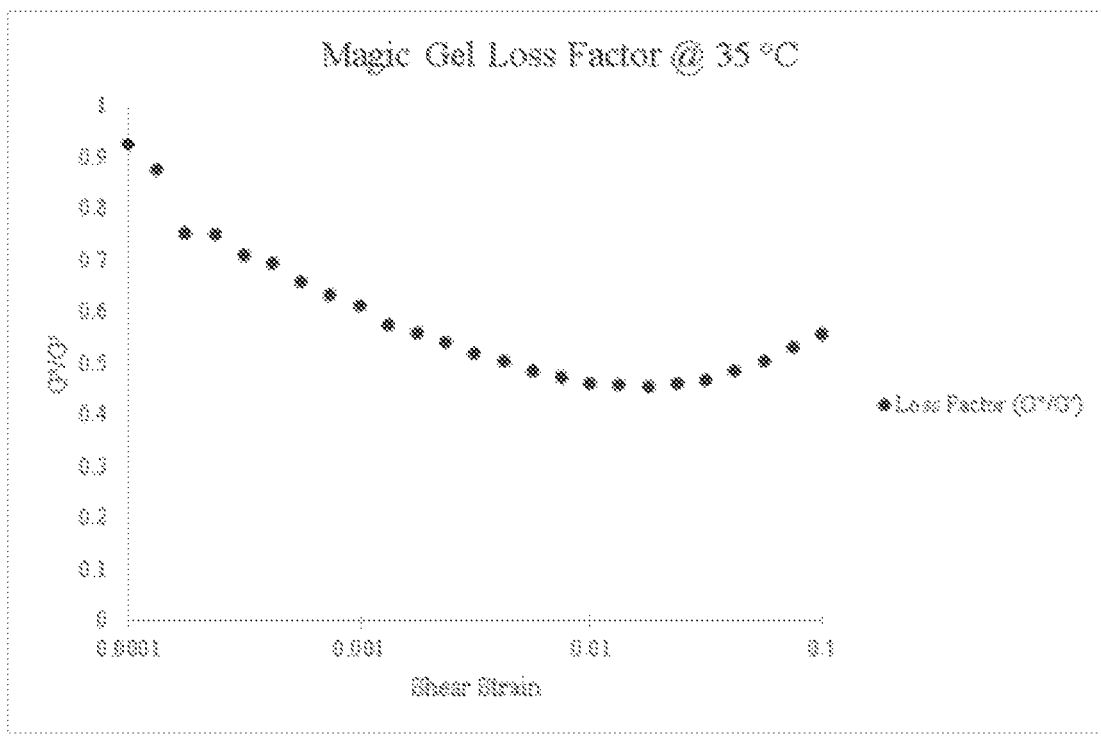
FIG. 5(d) is a graph of the loss factor for an embodiment of the thermo-responsive ultrasound coupling gel at 35° C.
Figure 5E:
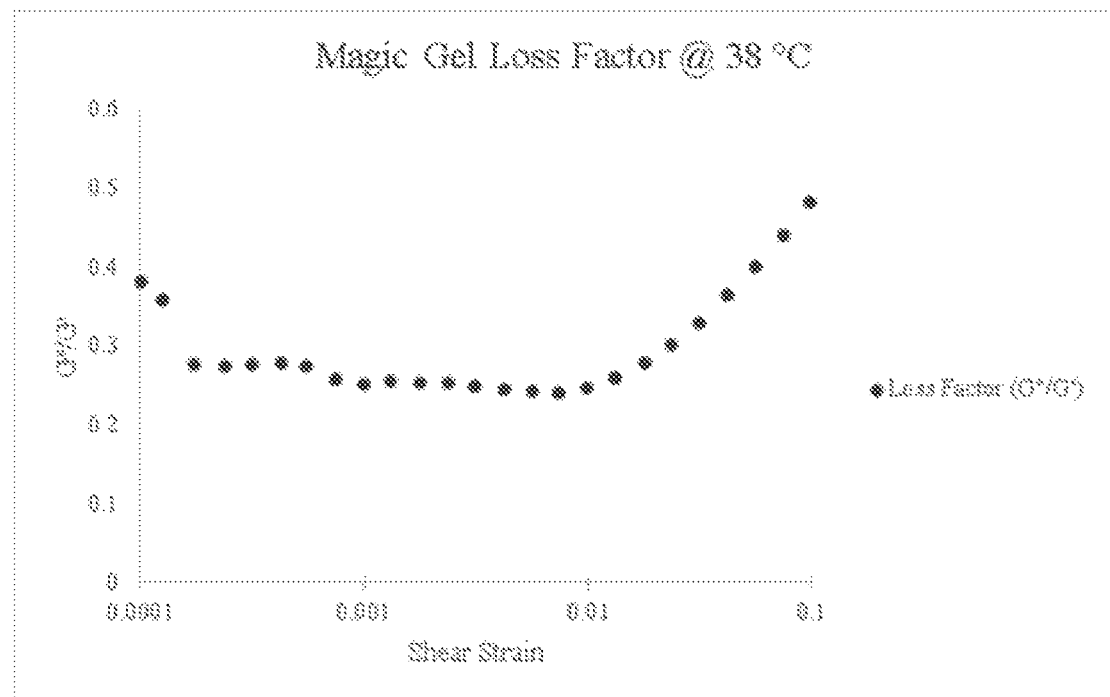
FIG. 5(e) is a graph of the loss factor for an embodiment of the thermo-responsive ultrasound coupling gel at 38° C.
Figure 6A:
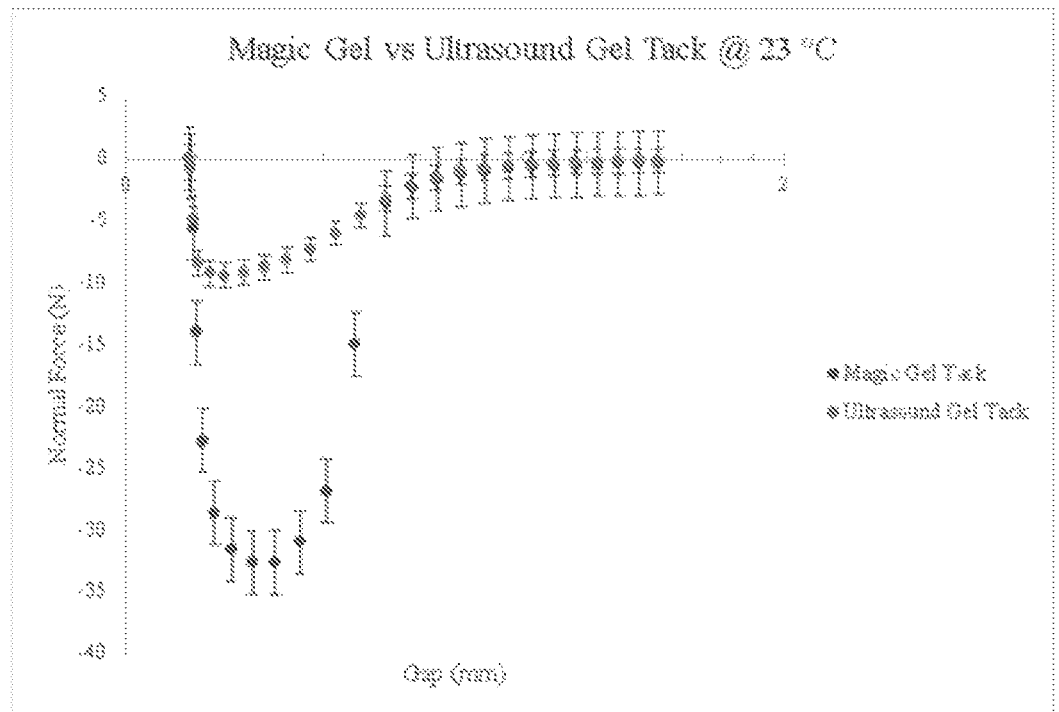
FIG. 6(a) is a graph comparing the tack of an embodiment of the thermo-responsive ultrasound coupling gel and a commercially available ultrasound coupling gel at 23° C.
Figure 6B:
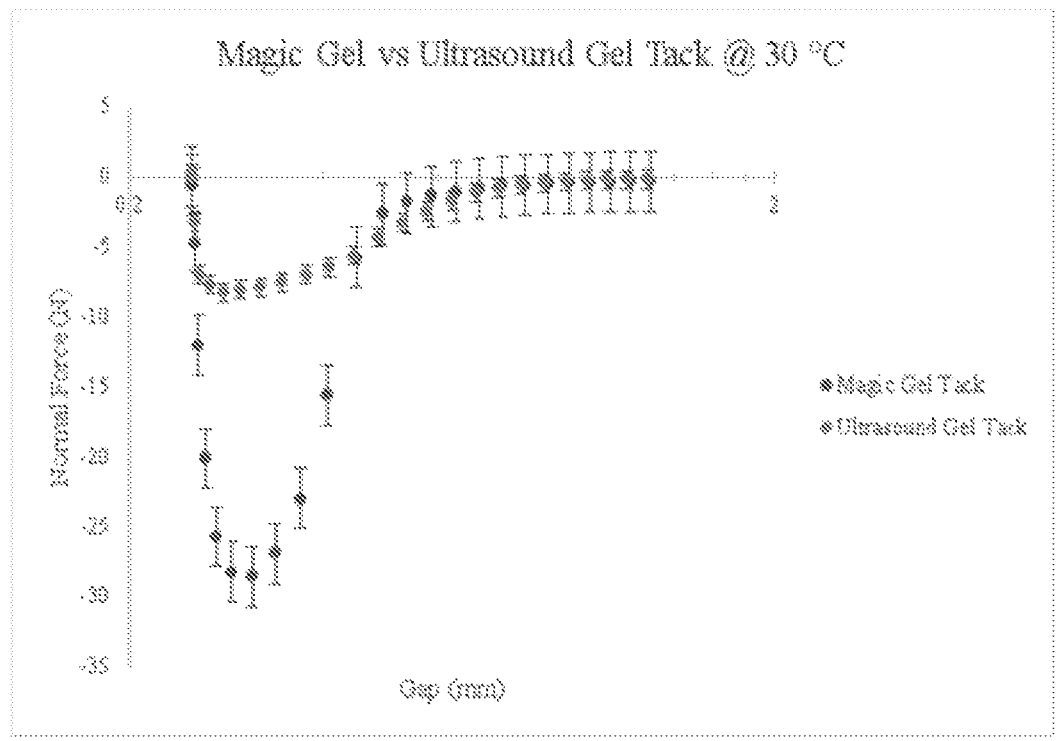
FIG. 6(b) is a graph comparing the tack of an embodiment of the thermo-responsive ultrasound coupling gel and a commercially available ultrasound coupling gel at 30° C.
Figure 6C:
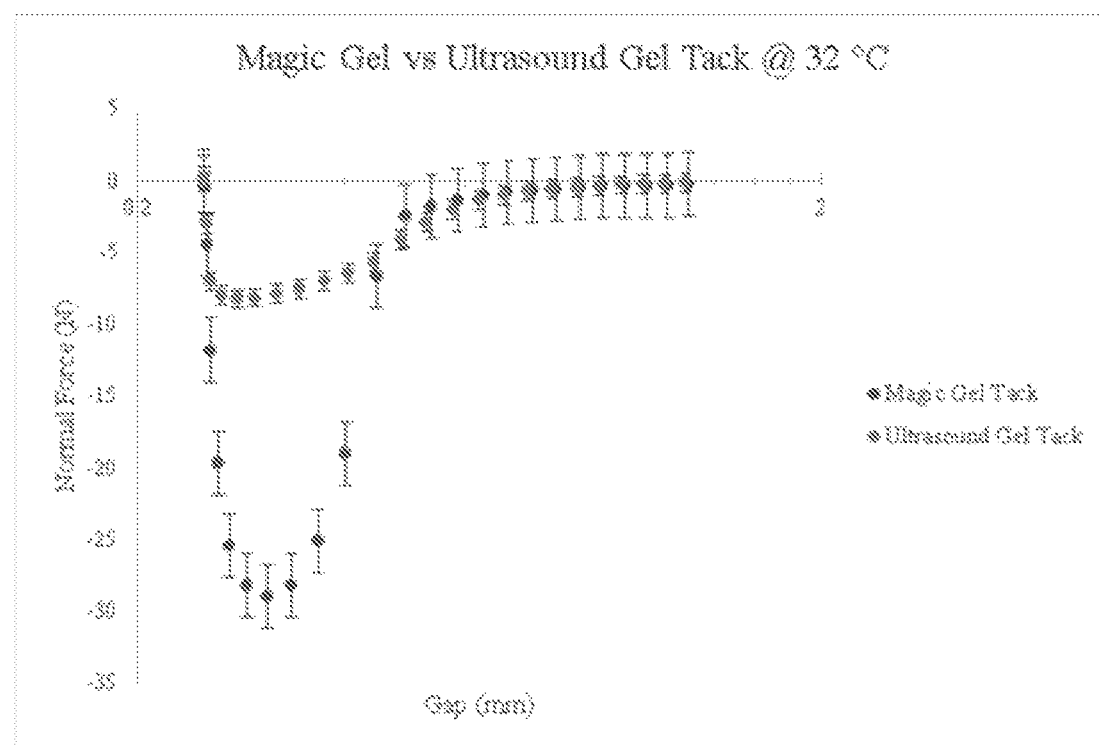
FIG. 6(c) is a graph comparing the tack of an embodiment of the thermo-responsive ultrasound coupling gel and a commercially available ultrasound coupling gel at 32° C.
Figure 6D:
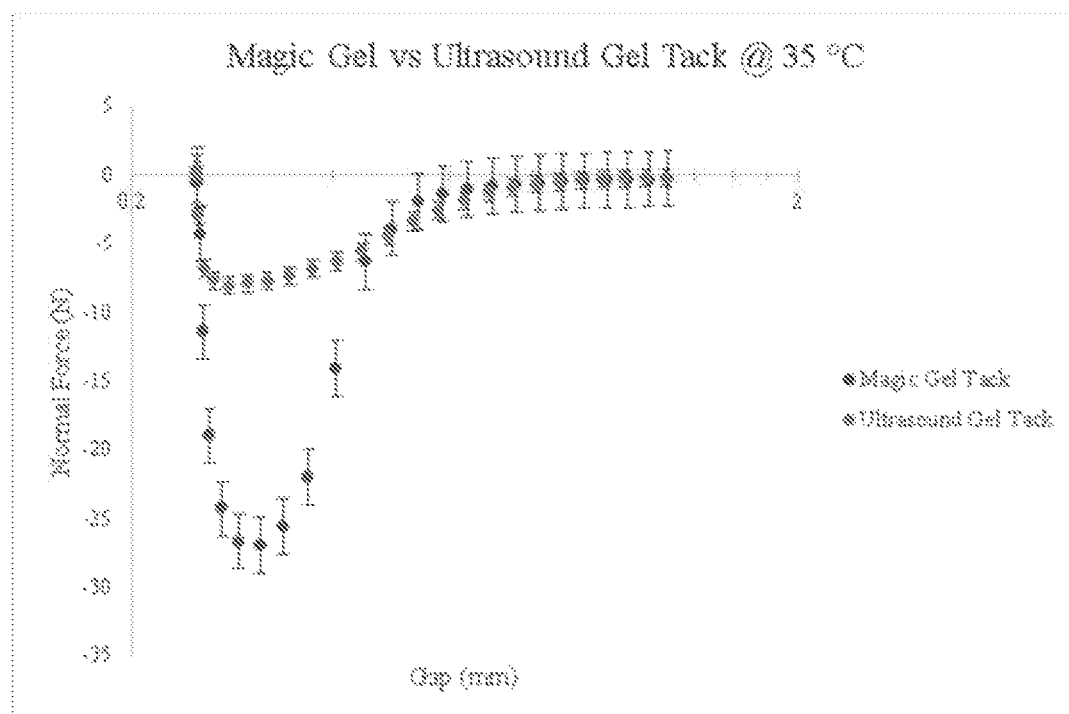
FIG. 6(d) is a graph comparing the tack of an embodiment of the thermo-responsive ultrasound coupling gel and a commercially available ultrasound coupling gel at 35° C.
Figure 6E:
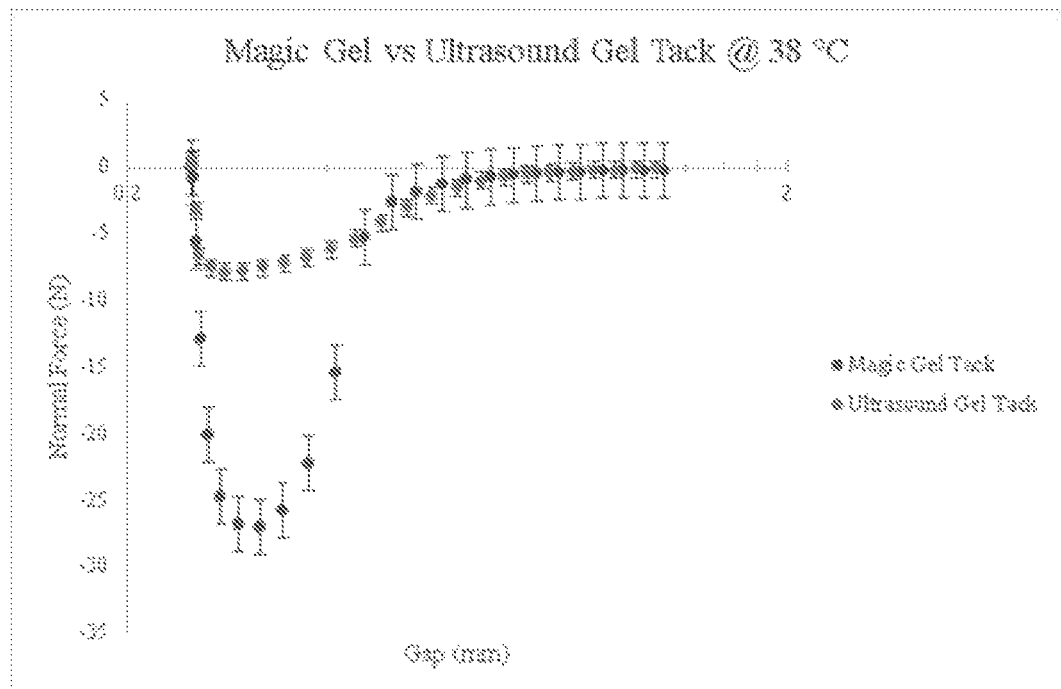
FIG. 6(e) is a graph comparing the tack of an embodiment of the thermo-responsive ultrasound coupling gel and a commercially available ultrasound coupling gel at 38° C.

Just as the moduli data showed, the magic gel performed in a manner very different from that of the standard ultrasound gel as observed through each of the progressing temperatures in the loss factor data. As FIGS. 5(a) and (b) show, the loss factor for the magic gel at 23° C. and 30° C. is well above 1, indicating a viscous dominant system that is present. FIG. 5(c) shows the magic gel beginning to approach the point of phase change as the loss factor begins to decrease considerably from its previous values at 30° C. It can be seen from FIG. 5(d) that the magic gel has transitioned to an elastic solid phase state by the time it reaches 35° C. and remains as such at 38° C. even with fluctuation in the actual loss factor. The loss factor data is more of an approximation of the phase state change that occurs within the magic gel than the storage and loss moduli data. As a result, the exact point of phase cross over that can be seen with the raw moduli data, appears as more of a range with the loss factor data but still works to reinforce and support the observation of the presence of the phase change within the magic gel that is not present within the standard ultrasound gel.

The tack test was conducted to demonstrate the difference in adhesive performance between the magic gel and standard ultrasound gel. This was specifically helpful in determining the temperature at which the reacted form of the magic gel would possess the greatest change in adhesive performance from the unreacted form at room temperature (i.e., 23° C.). It was also helpful in demonstrating the overall general enhanced adhesive performance of the magic gel as compared to that of standard ultrasound gel. As the FIGS. 6(a) to (e) show, the negative normal force experienced by the rheometer probe was greater for the magic gel than the standard ultrasound gel at each temperature by a significant margin. This is indicative of the stronger adhesive performance of the magic gel as compared to that of the standard ultrasound gel. It is also evidence that the magic gel possesses stronger viscous forces than standard ultrasound gel on a general scale. While the phase transitioning ability of the magic gel allows for controlled variability over the viscous properties of the gel, the magic gel possesses and overall greater adhesive strength while still allowing for clear signal transmissibility and intentional movement like with that of a probe during a procedure.

Figure 7:
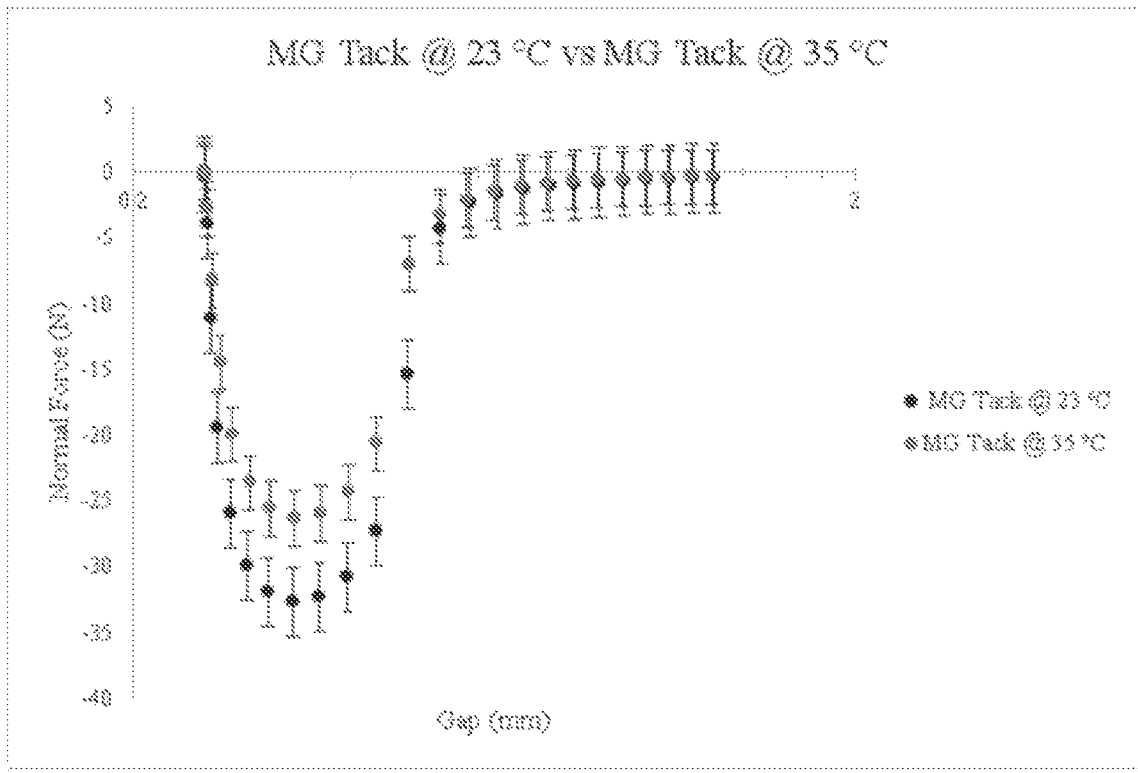
FIG. 7 is a graph comparing the adhesive force of an embodiment of the thermo-responsive ultrasound coupling gel at 23° C. and 35° C.

The magic gel also demonstrated its greatest difference in adhesive performance via tack at 32° C. and 35° C. FIG. 7 demonstrates the greatest differences in adhesive performance in the magic gel between its unreacted and reacted states. While the difference in the normal force present (23° C. vs 32° C.) is apparent, the difference in the normal force in FIG. 7 (23° C. vs 35° C.) is noticeably more significant as the magic gel progresses more into its elastic solid state from its initial viscoelastic liquid state. The larger difference in the normal force in FIG. 7 works to support both the moduli and loss factor data as it demonstrates the raw difference in force experienced by the gel as a result of the changing temperature and in conjunction a controlled phase state shift from a viscous dominant system to a more elastic dominant system. This is further evidence of the magic gel's ability to vary not only its viscoelastic properties but also its adhesive performance as a result of the higher applied temperature as compared to the constant and low adhesive performing nature of standard ultrasound gel.

Figure 8:
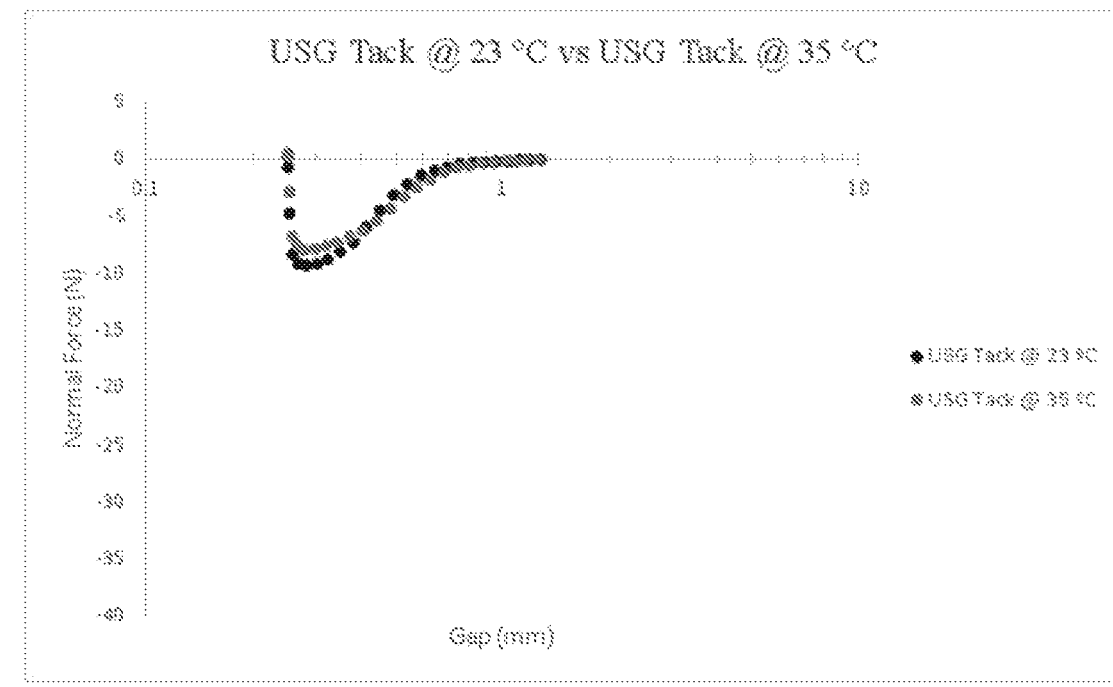
FIG. 8 is a graph comparing the adhesive force of a commercially available ultrasound coupling gel at 23° C. and 35° C.

As FIG. 7 shows, the magic gel experienced a greater negative normal force on average during the tack tests conducted with the magic gel at 23° C. than at 35° C. This is indicative of the gel's greater adhesive performance at 23° C., below the LCST before the physical crosslinking is triggered. The average highest normal force experienced by the magic gel at 23° C. was −32.492 N while the average highest normal force experienced by the magic gel at 35° C. was −26.136 N, meaning that there is approximately a 20% decrease in adhesive performance from the magic gel in its unreacted state to the magic gel in its reacted state. These results demonstrate the magic gel's variability in adhesive performance as a result of the physical crosslinking that takes place with the introduction of the correctly specified level of heat. A common phenomenon known as the temperature dependence of relaxation mechanisms in amorphous polymers describes the way in which the processes of temperature dependence of viscosity and mechanical relaxation in amorphous polymers is dependent on temperature through dependence on free volume (Williams, et al., 1955). This concept is commonly referred to as the reason for the reduction in the adhesive performance of a polymer as a result of increasing temperatures. This is not the case for the magic gel, however, as the physical crosslinking that takes place within the gel once the LCST has been eclipsed is responsible for the reduction in adhesive performance to the extent that the gel experiences. This is supported through the comparison of the magic gel tack test data to that of standard ultrasound gel seen in FIG. 8.

When viewed on the same scale as the magic gel's adhesive performance, it is clear that the standard ultrasound gel possesses an overall lower lever of adhesive performance at the same tested temperatures. Additionally, the overall percent difference in adhesive performance between the standard ultrasound gel at 23° C. and 35° C. is lower. The standard ultrasound gel experienced an average highest normal force of −9.3825 N during the tack tests at 23° C. and −8.015 N at 35° C., resulting in a 14% difference in adhesive performance from 23° C. to 35° C.

Figure 9:
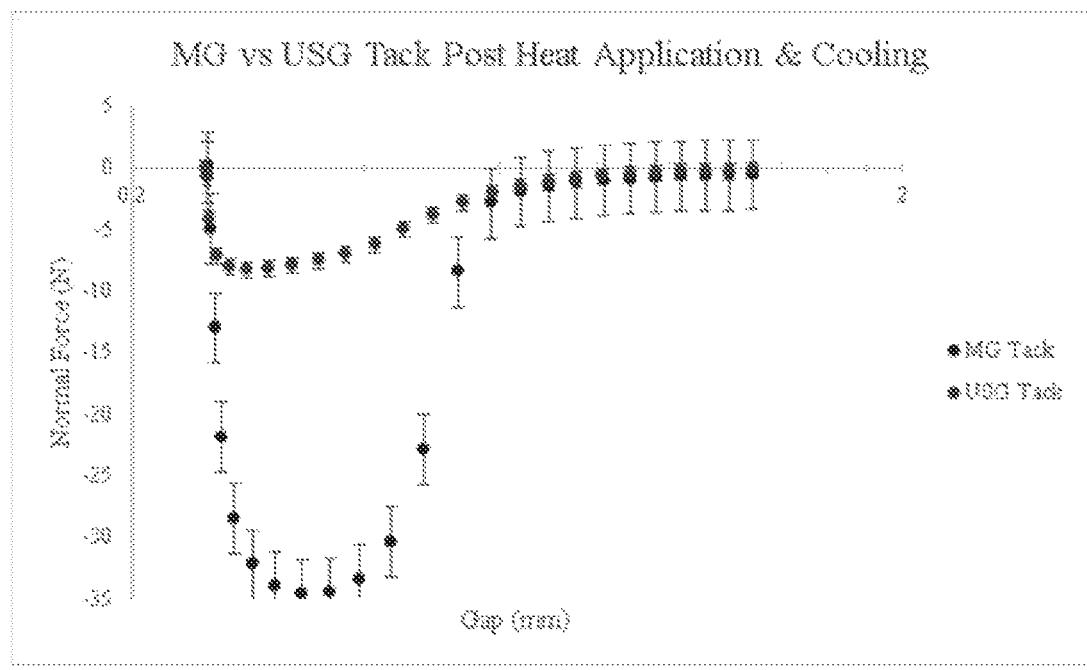
FIG. 9 is a graph comparing the tack of an embodiment of the thermo-responsive ultrasound coupling gel and a commercially available ultrasound coupling gel after heating and cooling.
Figure 10A:
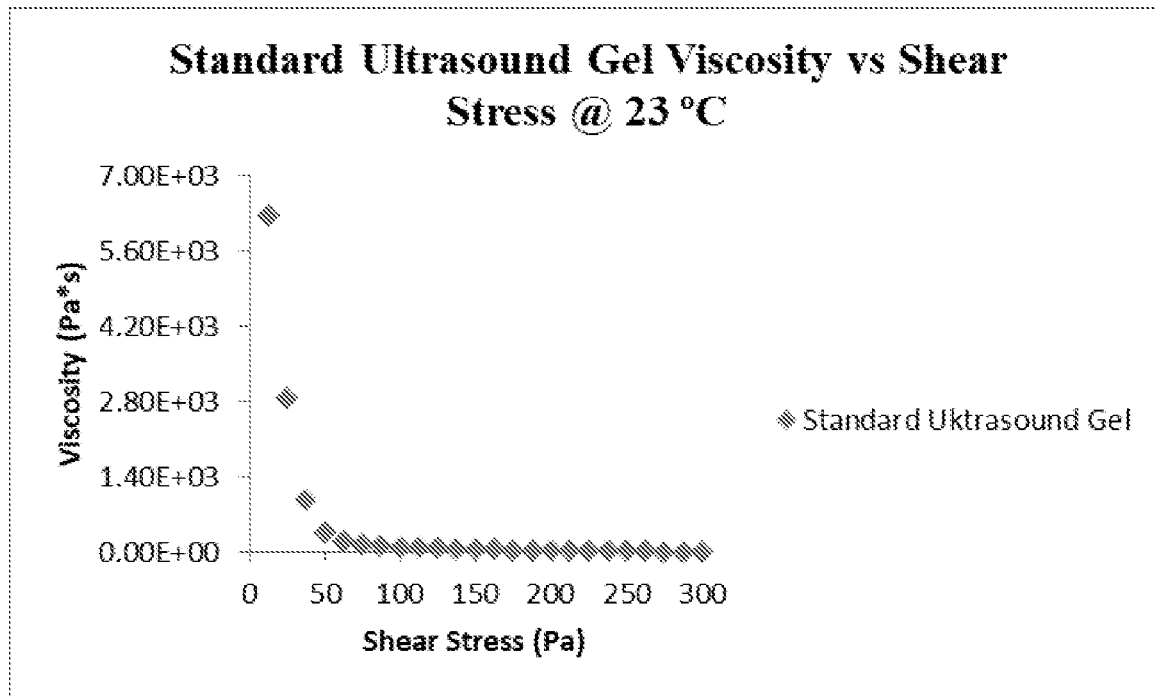
FIG. 10(a) is graph showing the viscosity and shear stress of a commercially available ultrasound coupling gel at 23° C.
Figure 10B:
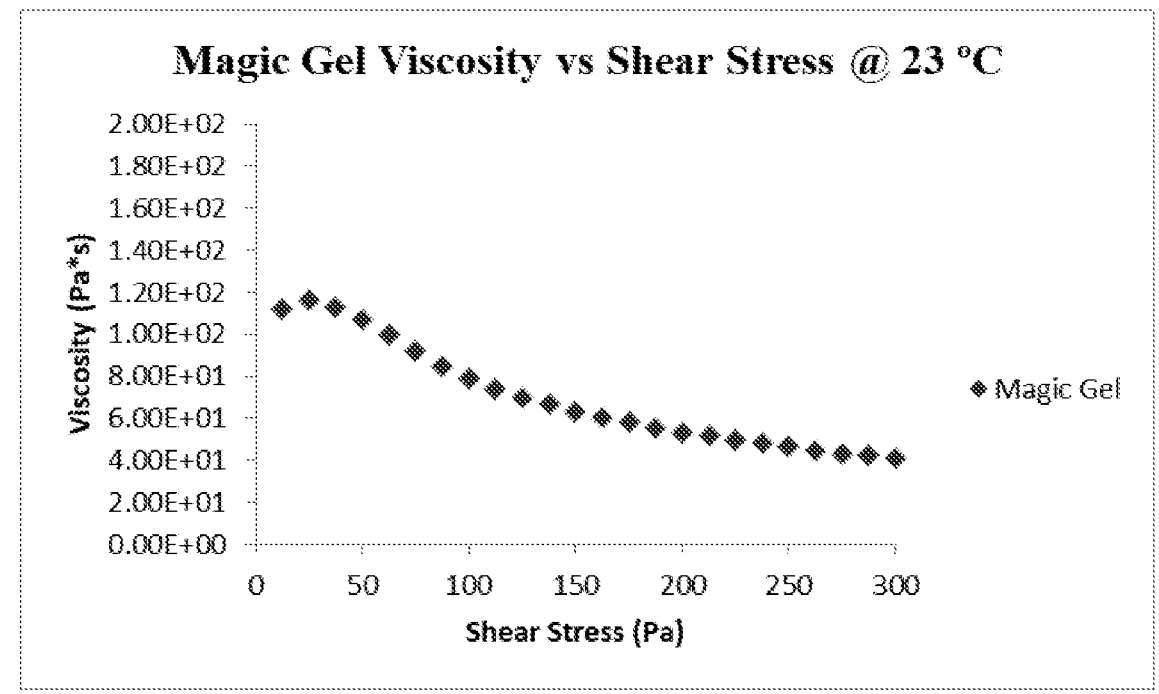
FIG. 10(b) is graph showing the viscosity and shear stress of an embodiment of the thermo-responsive ultrasound coupling gel at 23° C.
Figure 10C:
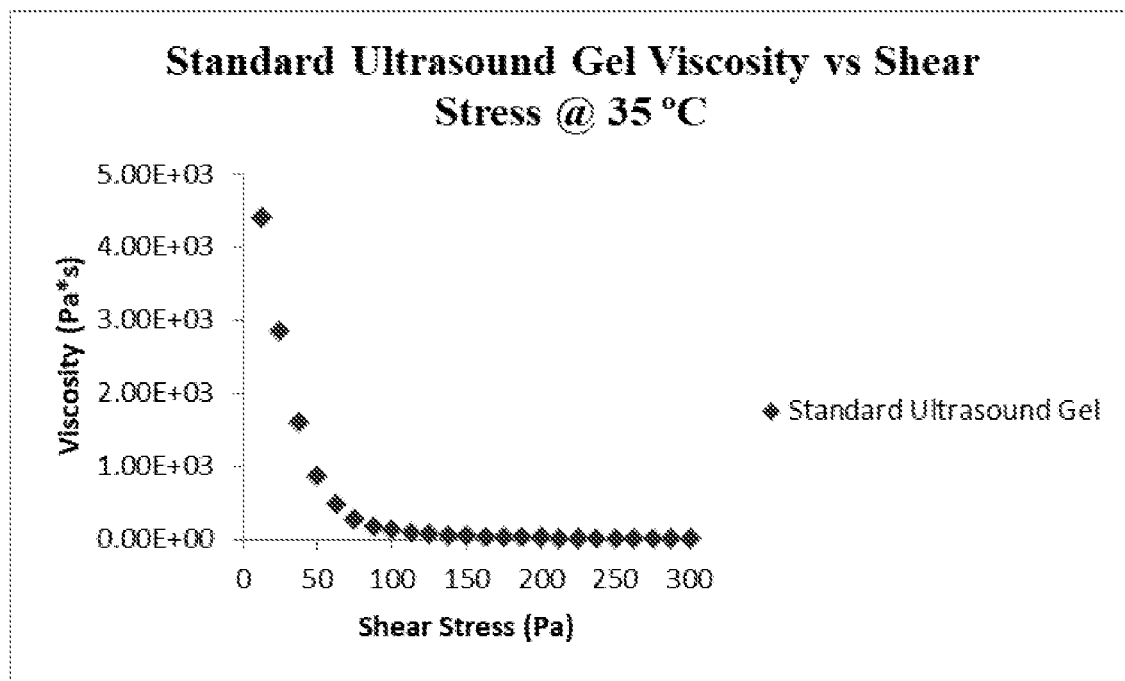
FIG. 10(c) is graph showing the viscosity and shear stress of a commercially available ultrasound coupling gel at 35° C.
Figure 10D:
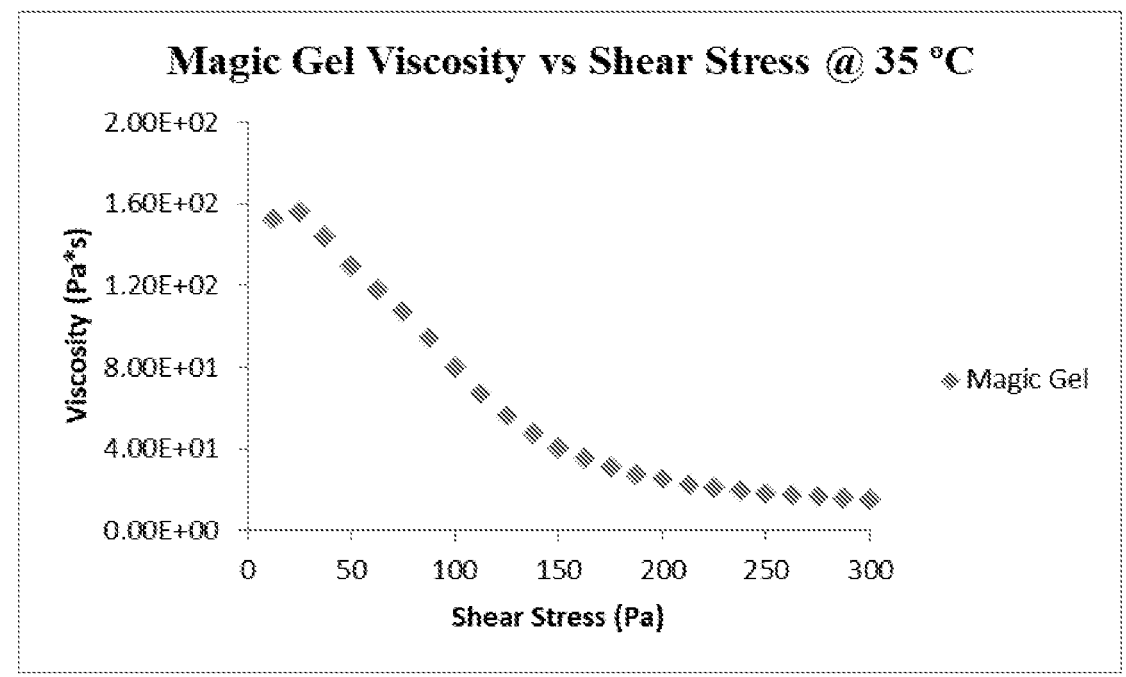
FIG. 10(d) is graph showing the viscosity and shear stress of an embodiment of the thermo-responsive ultrasound coupling gel at 35° C.

FIG. 9 shows that just as with the single temperature tack tests, the magic gel possessed an overall higher level of adhesive performance than that of the standard ultrasound gel when tested in combination with the temperature sweep loop from 23° C. to 35° C. and then back to 23° C. The magic gel had an average highest normal force of −34.6045 N while the standard ultrasound gel had an average highest normal force of −8.2935 N. These results indicate that the magic gel actually possessed a slightly higher level of adhesive performance once cooled back down to 23° C. than that of its original unreacted state, while the standard ultrasound gel actually possessed a slightly lower adhesive performance than that of the single temperature tack tests. The magic gel had in total 317% more adhesive performance than the standard ultrasound gel when the temperature sweep was applied to the tack test. The similar, and in this case even higher, level of adhesive performance that the magic gel displayed after being heated to its activation temperature and then cooled back to room temperature, in comparison to the single temperature tack tests suggests that the magic gel is capable of completing a full hysteretic cycle with respect to its adhesive performance manipulation through the application of heat. This is evidence that the adhesive performance of the magic gel can be reduced through the physical crosslinking via heat for the gel application part of the procedure, but that it can regain its full adhesive performance ability a short time after the gel application process to allow the probe to become and remain stabilized, effectively reducing probe drift during the main part of the procedure. The standard ultrasound gel again displayed its weak adhesive performance ability and did not demonstrate anything different from what was observed in the previous ultrasound gel samples that underwent tack tests. The standard ultrasound gel generally remains slick in the same capacity at all tested temperatures and did not seem to experience any type of hysteretic cycle as the magic gel did.

In order to compare the viscosities of the two gels, another rheometry test was conducted comparing a set range of shear stresses to the resulting viscosities for both the standard ultrasound gel and the magic gel. A test was conducted measuring a set interval of shear stress from 0-300 Pa against the resulting viscosity in order to examine the effect on the gel's viscosity. Both the standard ultrasound gel and the magic gel were subjected to shear stresses ranging from 0-300 Pa, resulting in a change to the particular gel's viscosity. This test was conducted for the standard ultrasound gel and the magic gel at two critical temperatures; the test was conducted at the room temperature of 23° C. for the standard ultrasound gel and the magic gel in its unreacted state as well as at 35° C. for the standard ultrasound gel and the magic gel in its reacted state. The results were indicative of the previously mentioned greater viscous properties of the magic gel as compared to that of the standard ultrasound gel. While the actual viscosity of the standard ultrasound gel started out as larger than that of the magic gel, the viscosity for the standard ultrasound gel quickly decreased with the increase of shear stress.

As FIGS. 10(a) to (d) demonstrates, while the standard ultrasound gel may begin with a large viscous value, the viscosity quickly declines as the shear stress is increased. While the magic gel also experiences a decrease in viscosity during the test, the viscosity decreases at a much slower rate than that of the standard ultrasound gel; eventually leveling out at viscosity twice as large as that of the standard ultrasound gel by the 300 Pa mark as shown in the following Table 1.

TABLE 1

| Shear Stress (Pa) | (a) Viscosity (Pa*s) | (b) Viscosity (Pa*s) | (c) Viscosity (Pa*s) | (d) Viscosity (Pa*s) |
| --- | --- | --- | --- | --- |
| 12.5 | 6250 | 112 | 4390 | 152 |
| 25 | 2870 | 116 | 2860 | 156 |
| 37.5 | 956 | 113 | 1600 | 144 |
| 50 | 360 | 107 | 868 | 129 |
| 62.5 | 204 | 99.8 | 478 | 118 |
| 75 | 147 | 92.2 | 283 | 107 |
| 87.5 | 116 | 85 | 183 | 94.3 |
| 100 | 96.1 | 78.9 | 129 | 80 |
| 112.5 | 80.9 | 74 | 96.7 | 66.8 |
| 125 | 69.1 | 70 | 75.9 | 55.9 |
| 137.5 | 59.1 | 66.4 | 61.2 | 47.3 |
| 150 | 50.3 | 63.2 | 49.9 | 40.6 |
| 162.5 | 42.4 | 60.4 | 40.9 | 35.5 |
| 175 | 35.5 | 57.8 | 33.3 | 31.3 |
| 187.5 | 29.7 | 55.4 | 27.2 | 27.8 |
| 200 | 24.9 | 53.3 | 22.3 | 25 |
| 212.5 | 21 | 51.4 | 18.4 | 22.8 |
| 225 | 17.8 | 49.6 | 15.2 | 21 |
| 237.5 | 15.2 | 47.9 | 12.8 | 19.5 |
| 250 | 13.1 | 46.3 | 11 | 18.3 |
| 262.5 | 11.4 | 44.7 | 9.55 | 17.5 |
| 275 | 9.96 | 43.3 | 8.22 | 16.75 |
| 287.5 | 8.74 | 42.1 | 7.22 | 16 |
| 300 | 7.69 | 40.9 | 6.35 | 15.4 |

Table 1 provides numerical data for the viscosity and shear stress tests comparing the standard ultrasound gel to the magic gel. In Table 1, (a) refers to the viscosity and shear stress for the standard ultrasound gel at 23° C.; (b) refers to the viscosity and shear stress for the magic gel at 23° C.; (c) refers to the viscosity and shear stress for the standard ultrasound gel at 35° C.; and (d) refers to the viscosity and shear stress for the magic gel at 35° C.

As Table 1 shows, the standard ultrasound gel responds to additional shear stress at a much greater rate than that of the magic gel leading to a greater decrease in viscosity given the same applied shear stress. This shows that the magic gel possesses the ability to achieve and sustain the same viscosity levels as that of standard ultrasound gel while maintaining an approximate viscosity level larger than that of the standard ultrasound gel given the same applied shear stress. These results demonstrate the ability of the magic gel to absorb a greater amount of applied shear stress while maintaining a greater functional viscosity than that of the standard ultrasound gel.

Image Quality

Figure 11A:
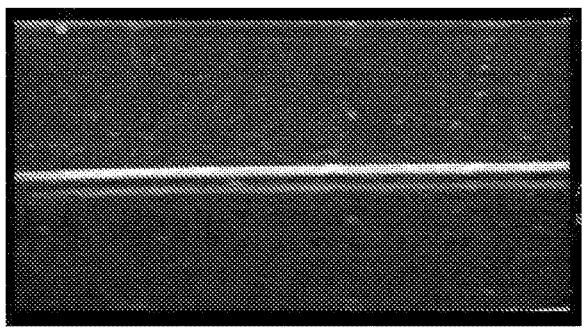
FIG. 11(a) is an ultrasound image showing a side view of an embodiment of the thermo-responsive ultrasound coupling gel on an ultrasound training simulation manikin.
Figure 11B:
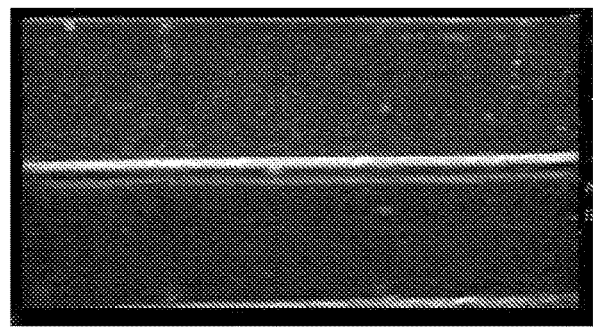
FIG. 11(b) is an ultrasound image showing a side view of a commercially available ultrasound coupling gel on an ultrasound training simulation manikin.
Figure 11C:
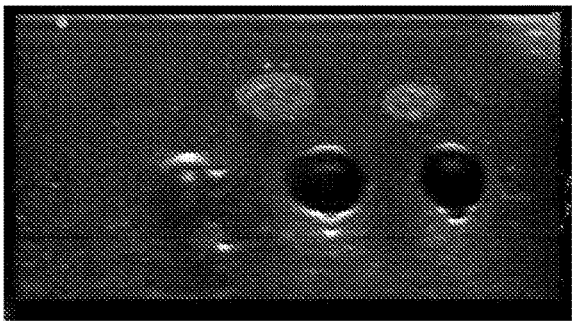
FIG. 11(c) is an ultrasound image showing a top view of the thermo-responsive ultrasound coupling gel at approximately 35° C. on an ultrasound training simulation manikin.
Figure 11D:
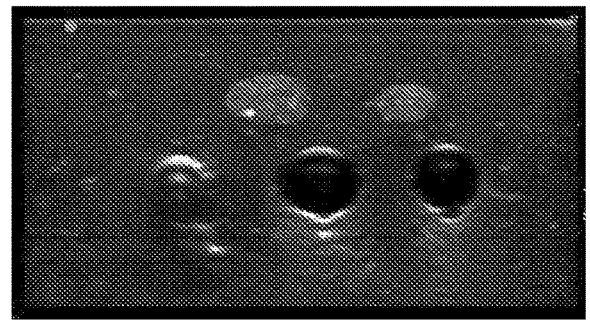
FIG. 11(d) is an ultrasound image showing a top view of a commercially available ultrasound coupling gel at room temperature on an ultrasound training simulation manikin.

The magic gel and a standard ultrasound gel were compared for attenuation and image quality using a blue ultrasound phantom. FIGS. 11(a) to (d) show ultrasound images of the blue phantom using the magic gel and the standard ultrasound gel. FIG. 11(a) shows a side view monitor image of the phantom when using the reacted form of the magic gel at approximately 35° C. as the coupling agent. FIG. 11(b) shows a side view monitor image of the phantom when using the standard ultrasound gel at room temperature as the coupling agent. FIG. 11(c) shows a front view monitor image of the phantom when using the reacted form of the magic gel at approximately 35° C. as the coupling agent. FIG. 11(d) shows a front view monitor image of the phantom when using the standard ultrasound gel at room temperature as the coupling agent.

Figure 12:
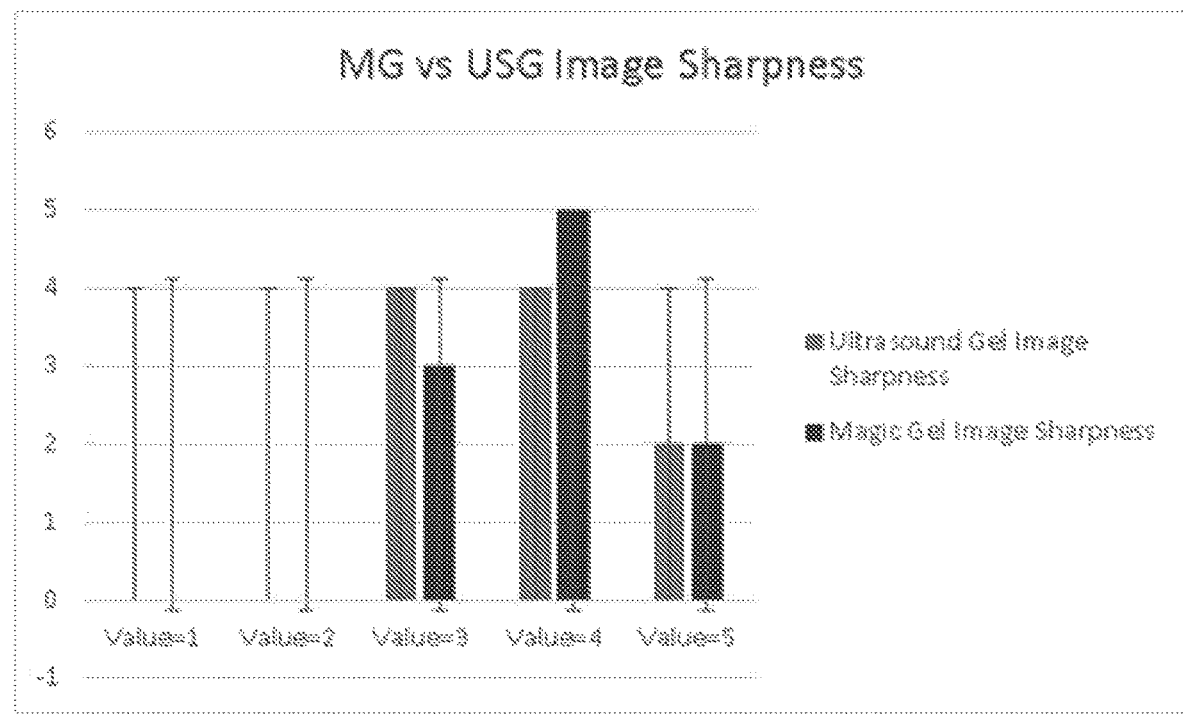
FIG. 12 is a graph comparing the image sharpness achieved in an ultrasound when using an embodiment of the thermo-responsive ultrasound coupling gel and a commercially available ultrasound coupling gel.
Figure 13:
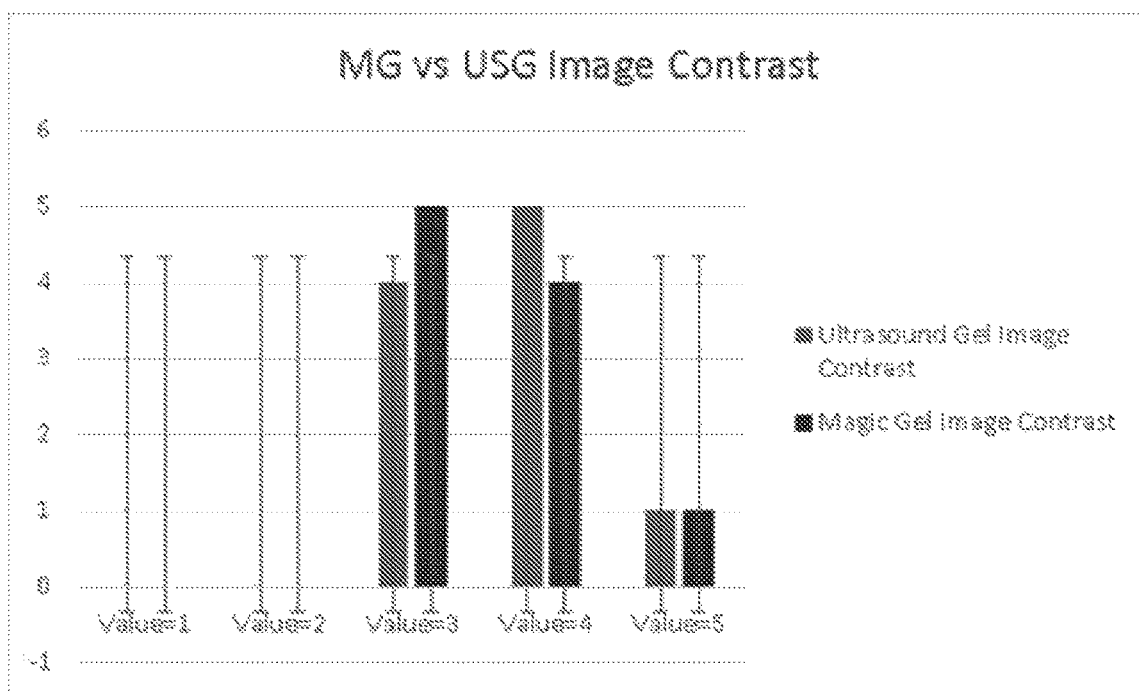
FIG. 13 is a graph comparing the image contrast achieved in an ultrasound when using an embodiment of the thermo-responsive ultrasound coupling gel and a commercially available ultrasound coupling gel.

Additionally, two sets of ten images of the magic gel and standard ultrasound gel were compared by blinded reviewers on a scale of 1-5, 1 being the worst and 5 being the best. The images were taken directly after the heat was applied to the magic gel and with no heat application to the standard ultrasound gel as it would normally be used. As FIGS. 12 and 13 show, there is little to no discernable difference in the image quality of the magic gel as compared to standard ultrasound gel. This is indicative of the magic gel's ability to transmit the ultrasound signal between the probe and the patient in the same capacity as that of standard ultrasound gel.

In the foregoing description, thermo-responsive ultrasound coupling gels, and methods and uses of such thermo-responsive ultrasound coupling gels of the present application have been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification, unless the context requires otherwise, the word "comprise" and its variations, such as "comprises" and "comprising," will be understood to imply the inclusion of a stated item, element or step or group of items, elements or steps, but not the exclusion of any other item, element or step or group of items, elements or steps. Furthermore, the indefinite article "a" or "an" is meant to indicate one or more of the item, element or step modified by the article.

The invention claimed is:

1. A method of conducting an ultrasound comprising:
   a) heating a thermo-responsive ultrasound coupling gel to a temperature≥35° C., the thermo-responsive ultrasound coupling gel comprising a thermo-responsive polymer solution that comprises
      1-10 wt % of a thermo-responsive polymer, and water,
      a solvent solution that comprises
      10-30 wt % of a solvent, and water, and
      a gelling agent solution that comprises
      10-30 wt % of a gelling agent, and water;
   b) applying the thermo-responsive ultrasound coupling gel to a patient at a temperature≥35° C.;
   c) cooling the thermo-responsive ultrasound coupling gel to a temperature<35° C.; and
   d) performing an ultrasound guided procedure, wherein the thermo-responsive ultrasound coupling gel is at a temperature<35° C.,
   wherein the thermo-responsive ultrasound coupling gel has a phase shift at a temperature in the range of 32 to 35° C. such that the gel has a loss factor G"/G' of >1 at <32° C. and a loss factor G"/G' of <1 at >35° C.

2. The method of claim 1, wherein the thermo-responsive ultrasound coupling gel has a tack in step a) and the thermo-responsive ultrasound coupling gel has a tack in step d) that is ≥20% of the tack in step a).

3. The method of claim 1, wherein the thermo-responsive ultrasound coupling gel comprises
   the thermo-responsive polymer solution that comprises
      4 wt. % of the thermo-responsive polymer, wherein the thermo-responsive polymer is poly (n-isopropyl acrylamide), and
      water,
   the solvent solution that comprises
      17 wt. % of the solvent, wherein the solvent is polyvinyl alcohol, and
      water, and
   the solvent solution that comprises
      20 wt. % of the gelling agent, wherein the gelling agent is hydroxy (propylmethyl) cellulose, and
      water, and
   wherein the weight ratio of the thermo-responsive polymer solution to the solvent solution to the gelling agent solution is 1:1:1.

4. The method of claim 1, wherein the thermo-responsive polymer is poly (n-isopropyl acrylamide).

5. The method of claim 1, wherein the solvent is selected from the group consisting of water, alcohols, and mixtures thereof.

6. The method of claim 1, wherein the gelling agent is selected from the group consisting of cellulose polymers, synthetic polymers, natural polymers, semi-synthetic polymers, and mixtures thereof.

7. The method of claim 1, wherein the solvent is polyvinyl alcohol.

8. The method of claim 1, wherein the gelling agent is present and is hydroxy(propylmethyl) cellulose.

9. The method of claim 1, wherein thermo-responsive ultrasound coupling gel further comprises an additional component selected from the group consisting of preservatives, antioxidants, fragrances, humectants, oils, emulsifiers, colorants, thickeners, stabilizers, binders, texturizers, pH control agents, and mixtures thereof.

10. The method of claim 1, wherein thermo-responsive ultrasound coupling gel comprises
    the thermo-responsive polymer solution that comprises
       3-5 wt. % of the thermo-responsive polymer, and water,
    the solvent solution that comprises
       16-18 wt. % of the solvent, and water, and
    the gelling agent solution that comprises
       19-21 wt. % of the gelling agent, and water.

11. The method of claim 1, wherein the weight ratio of the thermo-responsive polymer solution to the solvent solution to the gelling agent solution is 4-1:4-1:4-1.

* * * * *